US012653990B2

(12) United States Patent
Conlon

(10) Patent No.: US 12,653,990 B2
(45) Date of Patent: Jun. 16, 2026

(54) INTRAVASCULAR CATHETER HAVING A SINGLE THROUGH LUMEN AND A SEPARATE, INDEPENDENT, REMOVABLE FLUID CONDUIT DEVICE ASSEMBLABLE THEREIN

(71) Applicant: Neuravi Limited, Galway (IE)

(72) Inventor: Richard Conlon, Galway (IE)

(73) Assignee: NEURAVI LIMITED, Galway (IE)

( * ) Notice: Subject to any disclaimer, the term of this patent is extended or adjusted under 35 U.S.C. 154(b) by 904 days.

(21) Appl. No.: 17/930,316

(22) Filed: Sep. 7, 2022

(65) Prior Publication Data

US 2024/0075257 A1 Mar. 7, 2024

(51) Int. Cl.
| | |
|---|---|
| *A61M 25/10* | (2013.01) |
| *A61B 17/12* | (2006.01) |
| *A61M 25/00* | (2006.01) |

(52) U.S. Cl.
CPC . *A61M 25/10185* (2013.11); *A61B 17/12109* (2013.01); *A61B 17/12136* (2013.01); *A61M 25/0097* (2013.01)

(58) Field of Classification Search
CPC ..... A61M 2039/2426–2466; A61M 25/10186; A61M 25/10185; A61M 25/1025; A61M 25/0029; A61M 25/003; A61M 25/0032; A61M 2025/0035; A61M 2025/09166; A61M 25/0052; A61M 39/22; A61M 25/0074; A61M 25/0075; A61M 2025/0076; A61M 2025/1079; A61M 27/006; A61M 2039/0273; A61M 2205/32; A61M 25/0108; A61M 2039/027; A61M 2025/004; A61M 25/007; A61M 25/104; A61M 25/0021; A61M 25/0043; A61M 25/0105
USPC ................................. 604/103.1, 529, 103.04
See application file for complete search history.

(56) References Cited

U.S. PATENT DOCUMENTS

| | | | | |
|---|---|---|---|---|
| 3,726,283 | A | * | 4/1973 | Dye ................ A61M 25/09025 604/247 |
| 4,311,146 | A | | 1/1982 | Wonder |
| 4,327,734 | A | | 5/1982 | White, Jr. |
| 4,441,495 | A | | 4/1984 | Hicswa |
| 4,517,979 | A | | 5/1985 | Pecenka |
| RE32,348 | E | | 2/1987 | Pevsner |
| 4,646,742 | A | * | 3/1987 | Packard .......... A61M 25/10181 604/920 |

(Continued)

OTHER PUBLICATIONS

International Search Report & Written Opinion for counterpart PCT International Patent Application (PCT/IB2023/058818), Nov. 6, 2023 (16 pp.).

*Primary Examiner* — Cris L. Rodriguez
(74) *Attorney, Agent, or Firm* — Troutman Pepper Locke LLP

(57) ABSTRACT

An assemblable device including an intravascular catheter with a catheter shaft having an outer wall defining a single through lumen from a proximal end to an opposite distal end; proximate the distal end a portion of the outer wall of the catheter shaft is a membrane valve with an opening defined therein. The catheter shaft is devoid, free of, and has no dedicated fluid/inflation lumen. Instead, a separate, independent, removable fluid conduit device having a fluid lumen defined therein is assemblable so as to be slidable in the single through lumen of the intravascular catheter.

6 Claims, 15 Drawing Sheets

(56) References Cited

U.S. PATENT DOCUMENTS

| | | | |
|---|---|---|---|
| 4,723,547 A | 2/1988 | Kullas et al. | |
| 5,085,636 A | 2/1992 | Burns | |
| 5,100,385 A * | 3/1992 | Bromander | A61M 25/104 604/99.03 |
| 5,181,921 A | 1/1993 | Makita et al. | |
| 5,683,410 A * | 11/1997 | Samson | A61M 25/0075 604/249 |
| 5,928,218 A | 7/1999 | Gelbfish | |
| 6,827,703 B1 * | 12/2004 | Ackerman | A61M 25/10 604/99.04 |
| 8,366,734 B2 | 2/2013 | Hardert | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,610,396 B2 | 4/2020 | Brister et al. | |
| 10,893,966 B2 | 1/2021 | Brooks et al. | |
| 11,813,421 B2 * | 11/2023 | Pinchuk | A61M 25/10185 |
| 11,957,855 B2 * | 4/2024 | Casey | A61M 25/104 |
| 2003/0163115 A1 * | 8/2003 | Gershowitz | A61M 25/10 604/509 |
| 2003/0163117 A1 * | 8/2003 | Ishii | A61M 25/104 604/523 |
| 2004/0002680 A1 * | 1/2004 | Ackerman | A61M 31/00 604/96.01 |
| 2004/0073162 A1 * | 4/2004 | Bleam | A61M 25/10 604/103 |
| 2006/0106361 A1 * | 5/2006 | Muni | A61B 5/416 623/1.11 |
| 2007/0276314 A1 | 11/2007 | Becker | |
| 2008/0243069 A1 * | 10/2008 | Krivoruchko | A61L 31/14 604/103.1 |
| 2009/0093758 A1 | 4/2009 | Gross | |
| 2012/0232479 A1 * | 9/2012 | Vo | A61M 25/0053 604/524 |
| 2013/0184644 A1 * | 7/2013 | Vo | A61M 25/005 604/103.09 |
| 2016/0015928 A1 * | 1/2016 | Northrop | A61M 25/0054 264/134 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |
| 2017/0296324 A1 | 10/2017 | Argentine | |
| 2017/0296325 A1 | 10/2017 | Marrocco et al. | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0304041 A1 | 10/2017 | Argentine | |
| 2017/0304097 A1 | 10/2017 | Corwin et al. | |
| 2017/0304595 A1 | 10/2017 | Nagasrinivasa et al. | |

(56)                    References Cited

U.S. PATENT DOCUMENTS

| | | |
|---|---|---|
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2022/0047285 A1* | 2/2022 | Chou ............... A61M 25/0053 |
| 2022/0061863 A1 | 3/2022 | Lorenzo et al. |
| 2023/0277805 A1* | 9/2023 | Chou ............... A61M 25/0054 |
| | | 604/529 |

* cited by examiner

215

230

205

1

INTRAVASCULAR CATHETER HAVING A SINGLE THROUGH LUMEN AND A SEPARATE, INDEPENDENT, REMOVABLE FLUID CONDUIT DEVICE ASSEMBLABLE THEREIN

FIELD OF THE INVENTION

The present invention relates to an intravascular catheter used in a vascular treatment procedure (e.g., during a thrombectomy procedure to remove an occlusion in a blood vessel i.e., a clot). In particular, the present invention is directed to an intravascular catheter (e.g., balloon guide catheter) having a single through lumen and a separate, independent, removable fluid conduit device assemblable therein.

DESCRIPTION OF RELATED ART

Balloon guide catheters are commonly used during intravascular treatment procedures. One commonly performed treatment is a thrombectomy procedure wherein the balloon guide catheter is used to temporarily arrest blood flow, to assist in the capture and removal of an occlusion, blockage, thrombus, or clot from a blood vessel using a mechanical retrieval device (e.g., stent retriever) and/or through aspiration. Some balloon guide catheters are known to have a through lumen and a separated, dedicated eccentrically arranged inflation lumen with a braid reinforcement structure wrapped below and above the inflation lumen. Such eccentric configuration may have an imbalance of shaft flexibility. It would be desirable to design an improved balloon guide catheter having a more balanced shaft flexibility for superior device trackability and kink resistance.

When designing the catheter shaft with a through lumen and eccentrically arranged inflation lumen several competing factors are taken into consideration. On the one hand, maximizing the inner diameter of the through lumen is desirable to universally accommodate support devices differing in outer diameter and increase aspiration efficiency to optimize potential capture of the clot during retrieval attempts. While on the other hand, doing so without increasing the outer diameter or reducing the wall thickness of the catheter shaft. One conventional approach to accommodate these competing factors while increasing the inner diameter of the through lumen is to reduce the cross-sectional area in the inflation lumen. However, this design solution undesirably increases the deflation time performance of the balloon.

Prior to introduction into the body, the conventional balloon guide catheter must be "prepped", that is, purged of residual air from the inflation lumen. Often this preliminary step requires multiple attempts making the process time consuming and not consistently purging 100% of the residual air. These and other factors make prepping of the balloon guide catheter an annoyance to the interventionalist having to perform these affirmative steps.

It would be desirable to design an improved intravascular catheter (e.g., a balloon guide catheter) having a single through lumen and a separate, independent, removable fluid conduit device having at least one fluid lumen assemblable within the single through lumen of the intravascular catheter, wherein the inner diameter of the single through lumen of the intravascular catheter is maximized without: (i) reducing the cross-sectional area of the fluid lumen; (ii) increasing the outer diameter/profile of the catheter shaft; and (iii) reducing the wall thickness of the catheter shaft. Furthermore, it would be desirable to design an improved intravascular catheter that is easier to prep by positively venting residual air therefrom and have a more balanced shaft flexibility, for superior device trackability and kink resistance.

SUMMARY OF THE INVENTION

An aspect of the present invention is directed to an improved intravascular catheter (e.g., a balloon guide catheter) having a single through lumen and a separate, independent, removable fluid conduit device with at least one fluid lumen (e.g., inflation lumen) defined therein assemblable within the single through lumen of the intravascular catheter, wherein the inner diameter of the single through lumen of the intravascular catheter is maximized without: (i) reducing the cross-sectional area of the fluid lumen; (ii) increasing the outer diameter/profile of the catheter shaft; and (iii) reducing the wall thickness of the catheter shaft. Furthermore, it would be desirable to design an improved catheter that is easier to prep by positively venting residual air therefrom and have a more balanced shaft flexibility for superior device trackability and kink resistance.

Another aspect of the present invention relates to an assemblable device including an intravascular catheter including a catheter shaft having an outer wall defining a single through lumen from a proximal end to an opposite distal end; proximate the distal end a portion of the outer wall of the catheter shaft is a membrane valve with an opening defined therein; and a separate, independent, removable fluid conduit device having a fluid lumen defined therein; the separate, independent, removable fluid conduit device is assemblable so as to be slidable in the single through lumen of the intravascular catheter.

Still another aspect of the present invention relates to a method for using an assemblable device comprising a balloon guide catheter including a catheter shaft having an outer wall defining a single through lumen from a proximal end to an opposite distal end; proximate the distal end a portion of the outer wall of the catheter shaft is a membrane valve with an opening defined therein; the membrane valve being covered by a balloon secured to an outer surface of the outer wall of the catheter shaft. The assemblable device further includes a separate, independent, removable fluid conduit device having a fluid lumen defined therein; the separate, independent, removable fluid conduit device is assemblable so as to be slidable in the single through lumen of the balloon guide catheter. Wherein, the method includes the step of navigating the balloon guide catheter to a position proximal a target occlusion. Then, the separate, independent, removable fluid conduit device is inserted into the single through lumen of the balloon guide catheter; wherein before and/or after insertion into the balloon guide catheter the separate, independent, removable fluid conduit device is prepped to purge residual air from the fluid lumen. The separate, independent, removable fluid conduit device is properly aligned within the balloon guide catheter. Inflation media is injected via the fluid lumen, through the opening of the membrane valve and into the balloon. Lastly, the separate, independent, removable fluid conduit device is withdrawn.

While still another aspect of the present invention relates to a method for using an assemblable device including an intravascular catheter with a catheter shaft having an outer wall defining a single through lumen from a proximal end to an opposite distal end; proximate the distal end a portion of the outer wall of the catheter shaft is a membrane valve with an opening defined therein. The assemblable device further includes a separate, independent, removable fluid conduit device having a fluid lumen defined therein; the separate, independent, removable fluid conduit device is assemblable so as to be slidable in the single through lumen of the intravascular catheter. Wherein, the method includes the step of navigating the intravascular catheter to a target site. Then, the separate, independent, removable fluid conduit device is inserted into the single through lumen of the intravascular catheter. The separate, independent, removable fluid conduit device is properly aligned within the intravascular catheter. Fluid media is injected via the fluid lumen, through the opening of the membrane valve. Lastly, the separate, independent, removable fluid conduit device is withdrawn.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

In the description, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

Figures 1A, 1B, 1C:
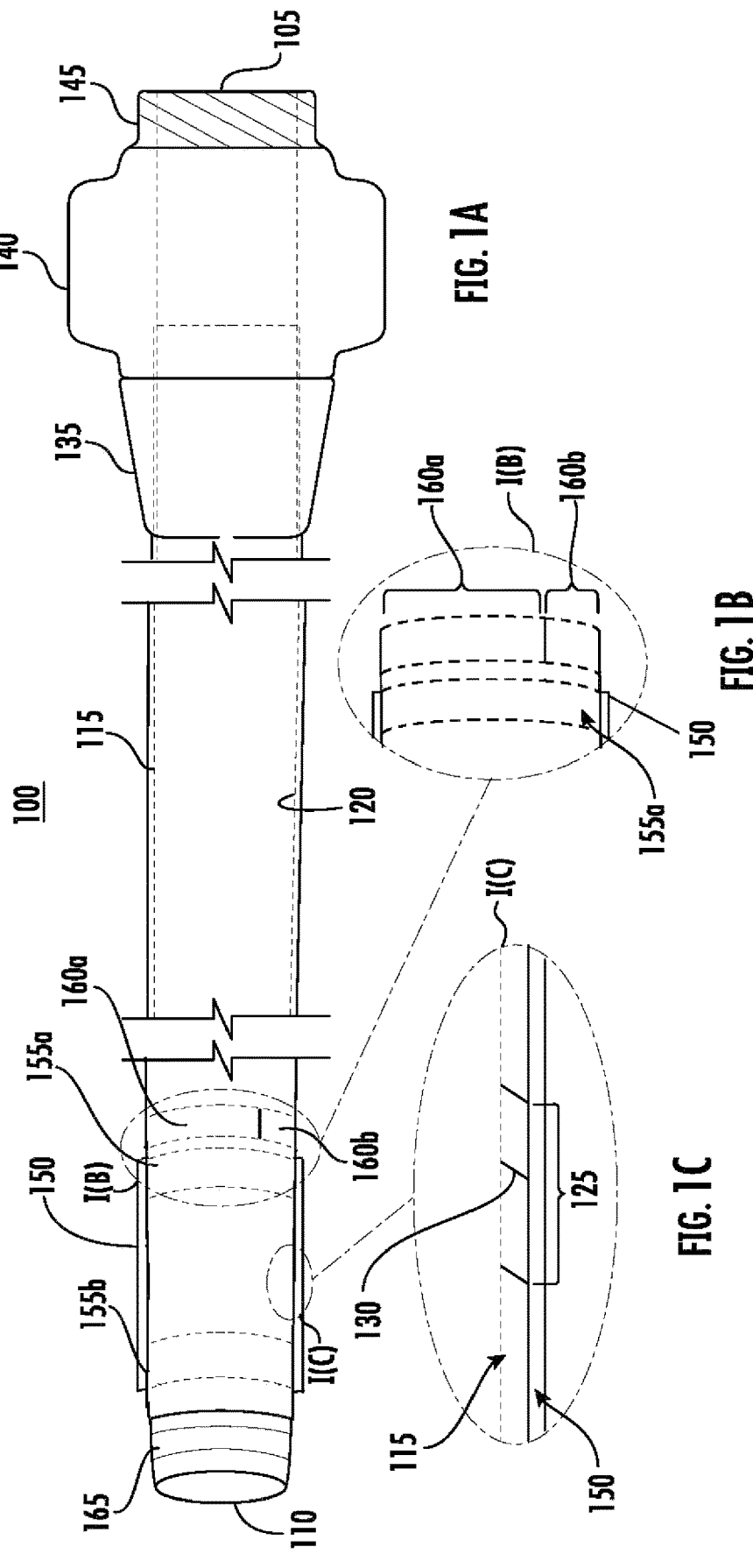
FIG. 1A is a side view of a first configuration of the present inventive balloon guide catheter having a single through lumen.
FIG. 1B is an enlarged view of section I(B) of the balloon guide catheter of FIG. 1A illustrating the radiopaque alignment marker associated therewith.
FIG. 1C is an enlarged view of section I(C) of the balloon guide catheter of FIG. 1A depicting the outer wall of the catheter shaft including a membrane valve with an X-shape cross-cut opening.

FIG. 1A depicts a configuration of the present inventive balloon guide catheter (BGC) 100 having a proximal end 105, an opposite distal end 110 with a single through lumen 120 defined axially/longitudinally therethrough for receiving a support device (e.g., a guidewire, a microcatheter and/or any other support device). That is, balloon guide catheter 100 is devoid, free of, and has no dedicated fluid/inflation lumen, only a single through lumen for receiving therein support devices. The balloon guide catheter 100 includes a catheter shaft 115 whose proximal end is assembled into a device hub 140 with a fluid tight seal (achieved by bonding or over-molding etc.). Preferably, a strain relief feature 135 is provided to prevent non-uniform curvature, i.e., "kinking" of the catheter shaft 115 at the junction between the device hub 140 and the catheter shaft 115. At the proximal end of the device hub 140 is a luer connection 145. Depicted in a deflated state, an elastomeric balloon 150 is secured (e.g., via a biocompatible adhesive or welded) to the outer surface of the catheter shaft 115 along respective proximal and distal radial bonds 155a, 155b. Covered by (i.e., radially inward of) the balloon 150, a section of the outer wall of the catheter shaft 115 is a membrane valve 125 made of a material more flexible than that of the material used to form the remaining portion of the outer wall of the catheter shaft 115. An opening 130 (e.g., X-shape cross-cut slit (depicted in the exemplary configuration of FIGS. 1A & 1C), tri-leaflet, bicuspid or slit) is defined in the membrane valve 125 through which inflation media passes therethrough during inflation/deflation of the balloon 150.

To ensure proper alignment, complementary alignment markers may be associated with each of the assembled components, i.e., the balloon guide catheter 100 and the separate, removable fluid conduit device 200 (described in detail further below). Alignment (in a radial direction and/or an axial/longitudinal direction) of the respective markers is indicative of proper positioning of the assembled components relative to each other to initiate injection/withdraw-of the injection fluid. Referring to the exemplary configuration in FIG. 1B, the alignment marker 160 associated with the balloon guide catheter 100 is disposed on the proximal side of the balloon 150 in the form of a partial (i.e., less than 360°) radial band section 160a made of a radiopaque material. Completing that 360° radial band the remaining radial section being a partial (i.e., less than 360°) radial band section 160b made of a non-radiopaque material. Preferably, a navigation marker 165 (e.g., a full or complete 360° radial band) made of a radiopaque material is disposed on the opposite distal side of the balloon 150 to assist with device navigation during tracking of the balloon guide catheter 100 to the target site in the vessel, but has no bearing on the alignment between the two components (e.g., the balloon guide catheter relative to the separate, removable fluid conduit device).

Since the balloon guide catheter 100 in FIG. 1A does not have (i.e., without or free of) a dedicated, separate fluid lumen (e.g., inflation lumen) the inner diameter of the single dedicated through lumen 120 therein may be maximized without increasing the outer diameter/profile or reducing the outer wall thickness. For instance, balloon guide catheter

100 may have an outer diameter range of 0.092" (7 Fr)-0.118" (9 Fr) and an inner diameter range of 0.067" (5.1 Fr)-0.093" (7.1 Fr). As a result of eliminating the dedicated fluid lumen, the balloon guide catheter 100 is suitable to universally accommodate via the single through lumen support devices having a wide range of outer diameters. In contrast to the conventional balloon guide catheter having a dedicated fluid lumen, the present inventive fluid conduit device 200 that is separate, independent and removable from that of the balloon guide catheter 100 of FIG. 1A is employed exclusively to deliver/withdraw fluid (e.g., inflation media) through the catheter, for example, to inflate/deflate the balloon 150.

Figure 2A:
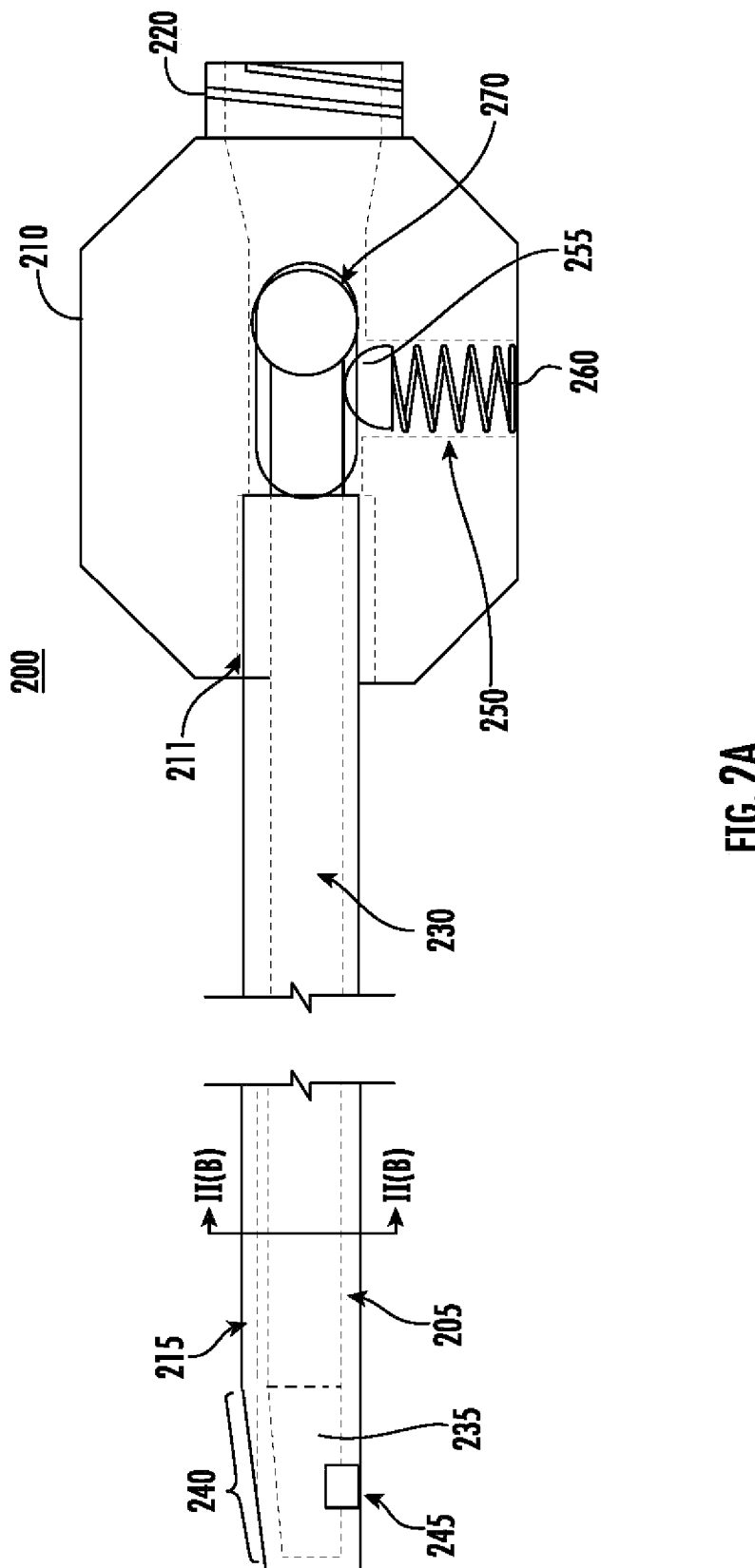
FIG. 2A is a longitudinal view of a first configuration of a fluid conduit device that is separate, independent, and removable so as to be assemblable within the single through lumen of the balloon guide catheter of FIG. 1A; wherein the separate, independent, removable fluid conduit device is depicted with a deployment mechanism in a disengaged state and an extendable fluid lumen in a retracted state.
Figure 2B:
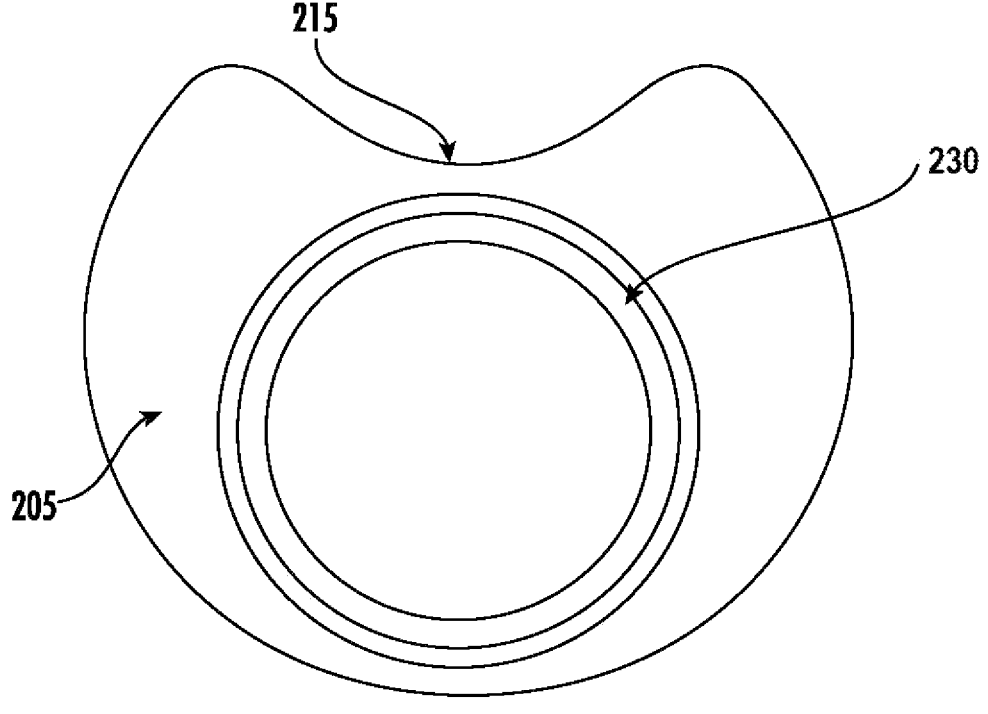
FIG. 2B is a radial cross-sectional view along lines II(B)-II(B) of the crescent shape outer profile of the shaft member of the separate, independent, removable fluid conduit device of FIG. 2A.
Figure 2C:
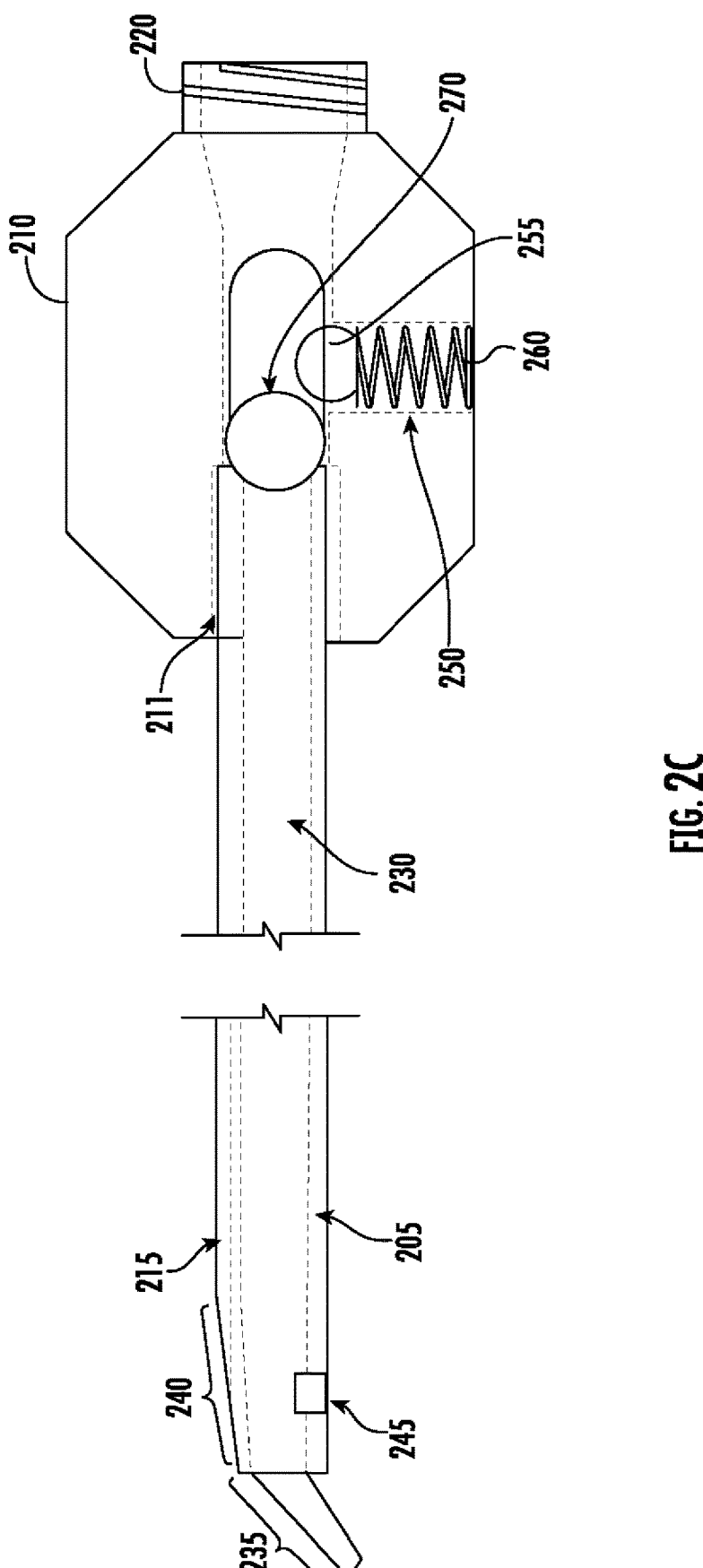
FIG. 2C is a longitudinal view of the separate, independent, removable fluid conduit device of FIG. 2A depicting the deployment mechanism in a deployed/engaged state and the associated extendable fluid lumen depicted in a fully deployed (lengthened) state with so that the distal tip is able to engage the opening in the membrane valve of the balloon guide catheter.

FIGS. 2A-2C depict a first configuration of the present inventive fluid conduit device 200 that is separate, independent, and removable from that of the balloon guide catheter 100 of FIG. 1A. When assembled in the single through lumen 120 of the balloon guide catheter device 100 of FIG. 1A, the separate, independent and removable fluid conduit device 200 in FIG. 2A is used to inject and/or withdraw a fluid (e.g., inflation media solution, such as a 50:50, radiopaque contrast agent and saline solution) in order to inflate/deflate the balloon 150. Fluid conduit device 200 includes a device hub 210 with a luer connection 220 at its proximal end and at its opposite distal end is attached (e.g., adhesive 211) to a shaft member 205. The shaft member 205 has an outer diameter sized to be receivable within the single through lumen 120 of the balloon guide catheter 100. Defined in the outer wall of the shaft member 205 is a single open channel, groove or furrow 215 extending in an axial/longitudinal direction sized to accommodate therein a support device (e.g., a guidewire and/or microcatheter). FIG. 2B depicts the crescent shaped radial cross-sectional view of the shaft member 205 of the fluid conduit device 200 along lines 11(B)-11(B). The single open channel, groove or furrow 215 starts from the proximal end of the shaft member section 205 and terminates at its distal end/tip a predetermined distance in a proximal direction relative to a distal end/tip of the shaft member 205 forming a tapered inner diameter distal section 240. That is, the single open channel, groove or furrow 215 does not extend into the tapered inner diameter distal section 240. As depicted in FIGS. 2A & 2C the inner diameter of the tapered inner diameter distal section 240 is angled (i.e., narrows) starting from a maximum inner diameter at its proximal end (i.e., the distal most end/tip of the single open channel, groove or furrow 215) to a minimum inner diameter at the distal most end/tip.

Along the outer profile of the shaft member 205 within the tapered inner diameter distal section 240 is located an alignment marker 245 associated with the separate, independent, removable fluid conduit device. In the example represented in FIG. 2A, the alignment marker 245 is a partial (i.e., less than 360°) radial marker band 245 made of a radiopaque material. Preferably, the radial arc and longitudinal/axial length of the partial radial marker band 245 is the same as that of the non-radiopaque partial radial band 160b of the balloon guide catheter 100. Accordingly, a state of proper alignment (both axially and radially) is realized when the partial radial band marker 245 of the separate, removable fluid conduit device 200 is aligned with the partial radiopaque radial band marker 160a of the balloon guide catheter 100, as visually observable via conventional imaging.

Disposed within the shaft member 205 of the separate, independent, removable fluid conduit device 200 is an extendable fluid lumen 230 (e.g., inflation lumen). The extendable fluid lumen 230 has a tapered outer diameter distal section 235 angled (i.e., narrows) starting from a maximum outer diameter at its proximal end to a minimum outer diameter at the distal most end/tip. Preferably, the slope of taper of the tapered inner diameter distal section 240 and tapered outer diameter distal section 235 match each other.

FIG. 2A depicts the extendable fluid lumen 230 of the separate, independent, removable fluid conduit device 200 in a non-deployed state (i.e., the tapered inner diameter distal section 235 fully retracted, fully sheathed, fully supported within the lumen of the shaft member 205). In response to engagement via a mechanical actuation device 250 (described in further detail below), the extendable fluid lumen 230 transitions to a fully deployed state with the tapered inner diameter distal section 235 (i.e., fully extended, fully lengthened, fully unsheathed, fully unsupported or fully unconstrained) out from the distal tip/end of the shaft member 205 (FIG. 2C). Prior to actuation, in a non-deployed state, the tapered inner diameter distal section 235 of the extendable fluid lumen 230 is fully sheathed (i.e., fully supported or fully constrained) within the lumen of the shaft member 205. When the balloon guide catheter 100 and separate, independent, removable fluid conduit device 200 are properly aligned, as previously described, once actuated, in a fully deployed (i.e., extended or lengthened) state (FIG. 2C), the tapered inner diameter distal section 235 of the extendable fluid lumen 230 is fully unsheathed from the shaft member 205. No longer supported or constrained within the lumen of the shaft member 205, the tapered inner diameter distal section 235 intentionally deflects downwards, directly physically contacting or directly physically engaging with the opening 130 (e.g., X-shape cross-cut slit) in the membrane valve 125 of the balloon guide catheter 100. Intentional deflection of the tapered inner diameter distal section 235 when no longer supported or constrained within the lumen of the shaft member 205 may be achieved in different ways. For instance, the extendable fluid lumen 230 may be made of a polymer material. During manufacture and prior to assembly in the shaft member 205 the desired curved/bent/deflected shape of the tapered inner diameter distal section 235 may be "set" using heat. While housed, supported or constrained in the shaft member 205, the curved/bent/deflected shape in the tapered inner diameter distal section 235 is elastically straightened. Once deployed (i.e., no longer housed, supported or constrained within the lumen of the shaft member 205) the tapered inner diameter distal section 235 automatically reverts/returns to the original "set" memory shape curved/bent/deflected configuration.

Mechanical actuation of the extendable fluid lumen section 230 may be accomplished in a variety of ways, for example, a ball-catch actuating mechanism 250, as depicted in FIGS. 2A & 2C. The exemplary ball-catch actuating mechanism 250 includes a ball 255 supported on a spring 260. To transition a switch 270 between states/positions (disengaged vs. engaged) spring 260 is compressed so that the ball 255 is out of the way permitting unhindered axial/longitudinal displacement in a distal direction of the switch 270 from the disengaged state/position (FIG. 2A) to the engaged state/position (FIG. 2C). Thereafter, the spring 260 is once again returned to an expanded state and the ball 255 seated thereon prevents axial/longitudinal movement thereby maintaining the engaged state/position of the switch 270 (FIG. 2C). Transition of the switch 270 from a disengaged state/position to an engaged state/position advances in a distal direction the tapered inner diameter distal section 235 of the extendable fluid lumen 230 out from the distal end of the shaft member 205 until the distal end/tip of the tapered inner diameter distal section 235 directly physically contacts or directly physically engages the opening 130 in the membrane valve 125 of the catheter shaft 115 of the balloon guide catheter 100. This direct engagement presupposes that the separate, independent, removable fluid conduit device 200 and balloon guide catheter 100 are in a state of proper alignment, as previously described in detail. FIG. 2C represents a longitudinal view of the fluid conduit device 200 of FIG. 2A illustrating the deflection/bending of the tapered inner diameter distal section 235 of the extendable fluid lumen 230 in a fully deployed/fully extended state in response to engaging the mechanical actuating mechanism 250. The tapered inner diameter distal section 235 of the extendable fluid lumen 230 automatically deflecting/bending toward the opening 130 in the membrane valve 125 as it advances in a distal direction through the tapered outer diameter distal section 240 of the shaft member 205.

Figure 3:
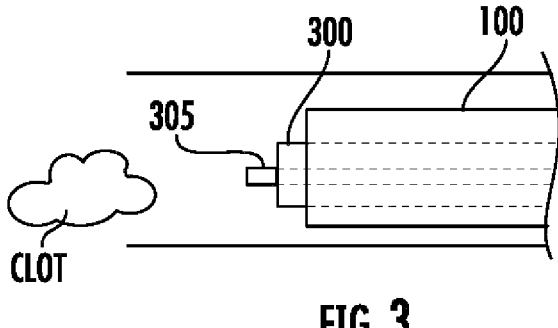
FIG. 3 is a longitudinal/axial side view of the balloon guide catheter having a single through lumen with a microcatheter advanced therein and a guidewire tracked through the passageway of the microcatheter; wherein the balloon guide catheter is depicted positioned at a target site in the vessel proximal to the target occlusion.
Figure 3A:
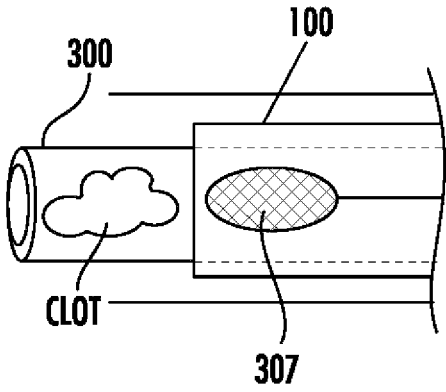
FIG. 3A is a longitudinal/axial side view of the balloon guide catheter of FIG. 3, following removal of the guidewire and introduction of a stent retriever into the lumen of the microcatheter.

In use, preferably employing a conventional introducer sheath (not shown), the interventionalist introduces the balloon guide catheter 100 (FIG. 1A) into the arterial system of the body, typically, via the femoral artery. The balloon guide catheter 100 is delivered within the vasculature to a target site (e.g., proximal of a target occlusion). As a single unit, a guidewire 305 disposed in a passageway of a microcatheter 300, is advanced together within the single through lumen of the balloon guide catheter 100 (FIG. 3). Next, either simultaneously or sequentially one after the other, the guidewire 305 and the microcatheter 300 emerges out from the distal end of the balloon guide catheter 100 and traverses the target occlusion (FIG. 3). Whereafter, the guidewire 305 is fully withdrawn and a stent retriever is delivered through the microcatheter 300 (FIG. 3A). The microcatheter 300 is then partially withdrawn while the stent retriever therein is maintained stationary. No longer sheathed within the microcatheter, the stent retriever automatically deploys across the clot which is captured and over time becomes embedded therein.

Figure 3B:
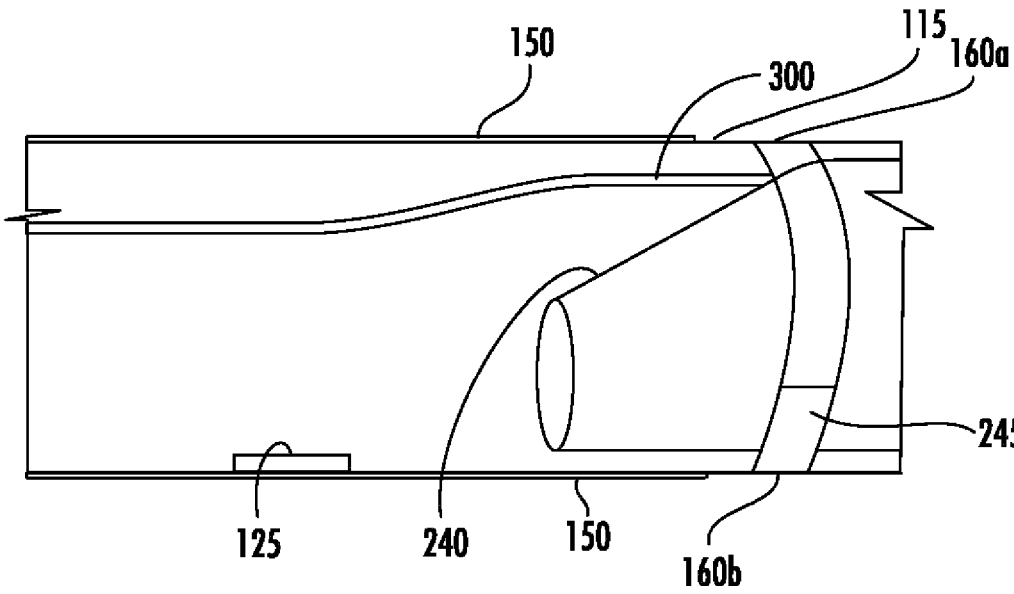
FIG. 3B is a partial view depicting the distal end/tip of the separate, independent, removable fluid conduit device of FIG. 2A assembled and properly aligned within the single through lumen of the balloon guide catheter (i.e., state of proper alignment of the respective radiopaque markers visible in the circled area), tracking over the microcatheter received in the open longitudinal channel/groove/furrow defined along the shaft member of the separate, independent, removable fluid conduit device; the balloon being depicted in the non-inflated state.

Outside the body, before assembly in the single through lumen 120 of the catheter shaft 115 of the balloon guide catheter 100, the separate, independent, removable fluid conduit device 200 is prepped to positively vent residual air from the fluid lumen 230 (e.g., inflation lumen). Specifically, using a syringe, a fluid (e.g., inflation media typically a 50:50 solution of radiopaque contrast agent and saline solution) is infused through the fluid lumen (e.g., inflation lumen) 230 until the fluid is observed emerging from the distal tip of the device, indicating all air has been exhausted. So long as the balloon 150, while in a deflated state, fits tightly to the outer surface of the catheter shaft 115 like a sleeve, then the balloon guide catheter 100, itself need not be prepped (i.e., purged of residual air). While maintaining the microcatheter 300 in position (i.e., without withdraw of the microcatheter) the separate, independent, removable fluid conduit device 200 is advanced in a distal direction through the single through lumen 120 of the balloon guide catheter 100 while tracking over the microcatheter 300 received within the single axial/longitudinal open channel/groove/furrow 215, as shown in FIG. 3B.

Figure 3C:
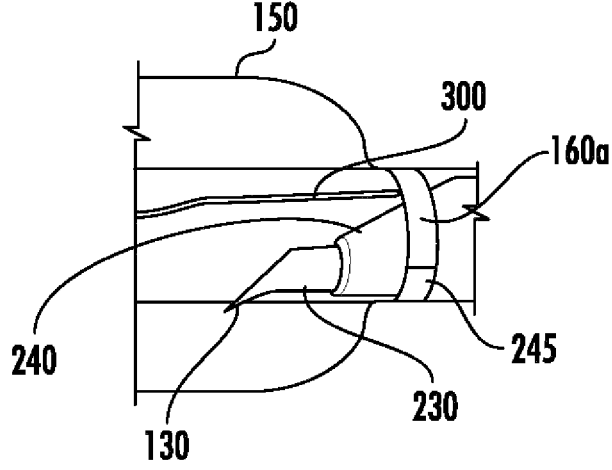
FIG. 3C is a partial view depicting the distal end/tip of the separate, independent, removable fluid conduit device of FIG. 2A, following assembly and proper alignment within the single through lumen of the balloon guide catheter; wherein the extendable fluid lumen of the separate, independent, removable fluid conduit device of FIG. 2A is in a fully deployed (extended or lengthened) state with the distal end/tip in direct physical contact/engagement with the X-shape cross-cut opening of the valve member integrated into the outer wall of the catheter shaft of the balloon guide catheter (visible within the circled area), so as to inflate the balloon.

Proper axial alignment of the separate, independent, removable fluid conduit device 200 within the balloon guide catheter 100 ensures that the distal end/tip of the tapered inner diameter distal section 235 of the extendable fluid lumen 230, when fully deployed, is in direct physical contact or direct physical engagement with the opening 130 in the membrane valve 125. Numerous ways to ensure proper axial alignment between the two components are contemplated. In the exemplary embodiment depicted in FIG. 3B the two assembled components (balloon guide catheter 100 and separate, independent, removable fluid conduit device 200) are in a state of proper alignment. Proper alignment is realized by advancing (e.g., sliding) the separate, independent, removable fluid conduit device 200 in a distal direction through the single through lumen 120 of the catheter shaft 115 of the balloon guide catheter 100 (while tracking over the microcatheter 300 accommodated within the single axial/longitudinal open channel, groove or furrow 215) until the separate, independent, removable fluid conduit device alignment marker 245 (e.g., radiopaque partial radial band marker section) associated with the separate, independent, removable fluid conduit device 200 is axially aligned with the catheter alignment marker 160*a* (e.g., radiopaque partial radial band marker section) of the balloon guide catheter 100. In other words, when aligned the separate, independent, removable fluid conduit alignment marker 245 (e.g., partial radial band of radiopaque material) overlaps with the non-radiopaque partial radial band marker section 160*b* (so as to be readily visible therethrough using conventional imaging) thereby fully completing (i.e., 360°) that radial band marker 160*a*, 245. Proper positioning of the two components (balloon guide catheter 100 and separate, independent, removable fluid conduit device 200) relative to each other ensures that the distal tip/end of the tapered inner diameter distal section 235 of the extendable fluid lumen 230, when in a fully deployed state, is in direct physical contact or direct physical engagement with the opening 130 (e.g., X-shape cross-cut slit) in the membrane valve 125 (FIG. 3C).

With the assembled components 100, 200 properly aligned, switch 270 of the separate, removable fluid conduit device 200 is placed in an engaged/deployed position (e.g., advanced in a distal direction) (FIG. 2C) resulting in advancement in a distal direction of the extendable fluid lumen section 230 out from the distal end of the shaft member 205. When fully deployed, the distal tip/end of the tapered inner diameter distal section 235 of the extendable fluid lumen 230 is in direct physical contact or direct physical engagement penetrating the opening 130 (e.g., X-shape cross-cut slit) of the membrane valve 125 (FIG. 3C). Fluid (e.g., inflation media solution) injected (e.g., via a syringe) into the separate, independent, removable fluid conduit device 200 passes first through the device hub 210 then through the deployed extendable fluid lumen 230. Fluid exiting from the distal end/tip of the tapered inner diameter distal section 235 of the extendable fluid lumen 230 passes through the opening 130 (e.g., X-shape cross-cut slit) in the membrane valve 125 and into the balloon 150.

Once the balloon is inflated, switch 270 is toggled to the disengaged state (e.g., retracted in a proximal direction) causing the tapered inner diameter distal section 235 of the extendable fluid lumen 230 to fully retract (disengage from the opening 130), as shown in FIG. 2A resulting in the opening 130 (e.g., X-shape cross-cut slit) in the membrane valve 125 automatically closing. While the extendable fluid lumen 230 is in a retracted state, the separate, independent, removable fluid conduit device 200 is fully withdrawn in a proximal direction, leaving in place the microcatheter 300 within the single through lumen 120 of the balloon guide catheter 100. Lastly, the microcatheter 300 in combination with the stent retriever 307 having the target occlusion embedded therein is withdrawn in a proximal direction through the single through lumen 120 of the balloon guide catheter 100, optionally while subject to aspiration.

Following capture and removal of the target occlusion, subsequent steps are directed to deflating the balloon 150.

Figure 3D:
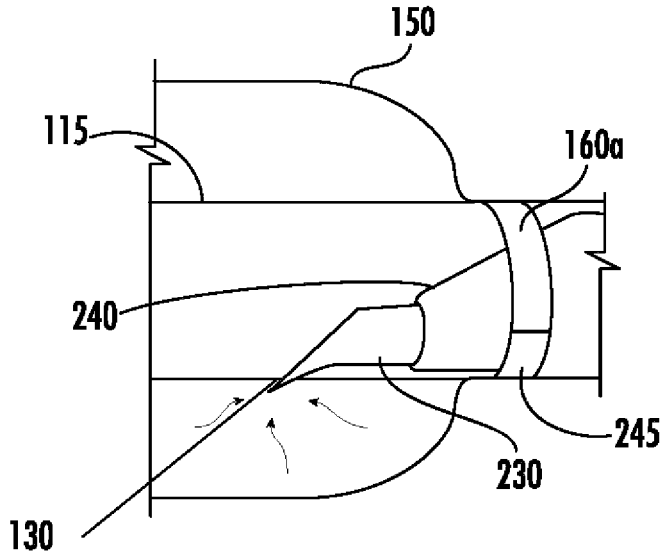
FIG. 3D is a partial view, similar to that in FIG. 3C (during inflation of the balloon), but here depicted during subsequent deflation of the balloon, wherein the distal end/tip of the separate, independent, removable fluid conduit device of FIG. 2A following reassembly is properly aligned within the single through lumen of the balloon guide catheter; and wherein the extendable fluid lumen of the fluid conduit device of FIG. 2A is in a fully deployed (extended or lengthened) state with the distal end/tip in direct physical contact/engagement with the X-shape cross-cut opening of the valve member integrated into the wall of the catheter shaft, of the balloon guide catheter, permitting the inflation media to be aspirated therethrough and deflate the balloon (as represented by the arrow lines)

This is accomplished by reintroducing the separate, independent, removable fluid conduit device 200 in a distal direction into the single through lumen 120 of the balloon guide catheter 100 until once again proper alignment is achieved among the two components, e.g., alignment of the respective radiopaque markers 245, 160*a* as described in detail above during inflation of the balloon. Switch 270 is once again toggled to an engagement/deployed position advancing the extendable fluid lumen 230 until the distal tip/end of the tapered inner diameter distal section 235 is in direct physical contact or direct engagement against/penetrates the opening 130 (e.g., X-shape cross-cut slit) of the membrane valve 125 (FIG. 3D). Vacuum or negative pressure is applied to the fluid lumen of the separate, independent, removable fluid conduit device 200 purging the fluid (e.g., inflation media solution) from inside the balloon 150 causing it to deflate.

Once the balloon 150 is deflated, switch 270 is toggled to the disengaged state (e.g., retracted in a proximal direction) causing the tapered inner diameter distal section 235 of the extendable fluid lumen section 230 to fully retract into the shaft member 205. Thereafter, the separate, independent, removable fluid conduit device 200 is fully removed (i.e., withdrawn in a proximal direction) from the single through lumen 120 of the balloon guide catheter 100. Recanalization of the artery may be determined by any available imaging (e.g., conventional transfemoral angiography (CTA), magnetic resonance angiography (MRA), or transcranial Doppler sonography). If sufficient recanalization is measured, the balloon guide catheter is then also fully withdrawn in a proximal direction from the body.

The present inventive separate, independent, removable fluid conduit device having an axial/longitudinal open channel, groove or furrow defined therein has been described above for the particular use or application as an inflation lumen for injection/extraction of an inflation media used to inflate/deflate a balloon of a balloon guide catheter. It is contemplated and within the intended scope of the present invention for any configuration of the present inventive separate, independent, removable fluid conduit device to be employed with single through lumen catheters without a balloon (i.e., other than balloon guide catheters). For instance, the present inventive separate, independent, removable fluid conduit device may be used to administer a contrast media (e.g., dye such as gadolinium contrast media used during magnetic resonance imaging) to improve diagnostic results during imaging procedures. The single axial/longitudinal open channel, groove or furrow permits introduction of the separate, independent, removable fluid conduit device into the single through lumen of the catheter without requiring the removal of the microcatheter (i.e., maintaining the microcatheter stationary in place). Thus, the present inventive single axial/longitudinal open channel, groove or furrow configuration of the separate, independent, removable fluid conduit device may be employed with other catheters.

While yet another configuration of the present inventive separate, independent, removable fluid conduit device 500 is illustrated, by way of example, in use with a balloon guide catheter 400 having a single through lumen 420 defined axially/longitudinally therethrough from a proximal end 405 to an opposite distal end 410 is described in connection with FIGS. 4 & 5A. A balloon 450 (depicted in FIG. 4 in a deflated state) is secured (e.g., adhered or welded) via respective proximal and distal radial bonds 455, 455' about the outer surface of a catheter shaft 415 of the balloon guide catheter 400 covering a membrane valve 425 having an opening 430 (e.g., X-shape cross-cut slit, tri-leaflet, bicuspid or slit) defined therein, integral with or secured to the outer wall of the catheter shaft. A proximal end 405 of the catheter shaft 415 is connected to a device hub 440 having a side arm/port 470 and though port 445 connectable to a removable Tuohy Borst adapter/valve 475. The balloon guide catheter has a navigation marker (e.g., radiopaque radial band marker) 465 proximate the distal end/tip. This navigation marker being useful during fluorographic imaging to ensure proper positioning of the distal end of the balloon guide catheter 400 at the target site in the patient's vessel.

Figure 4:
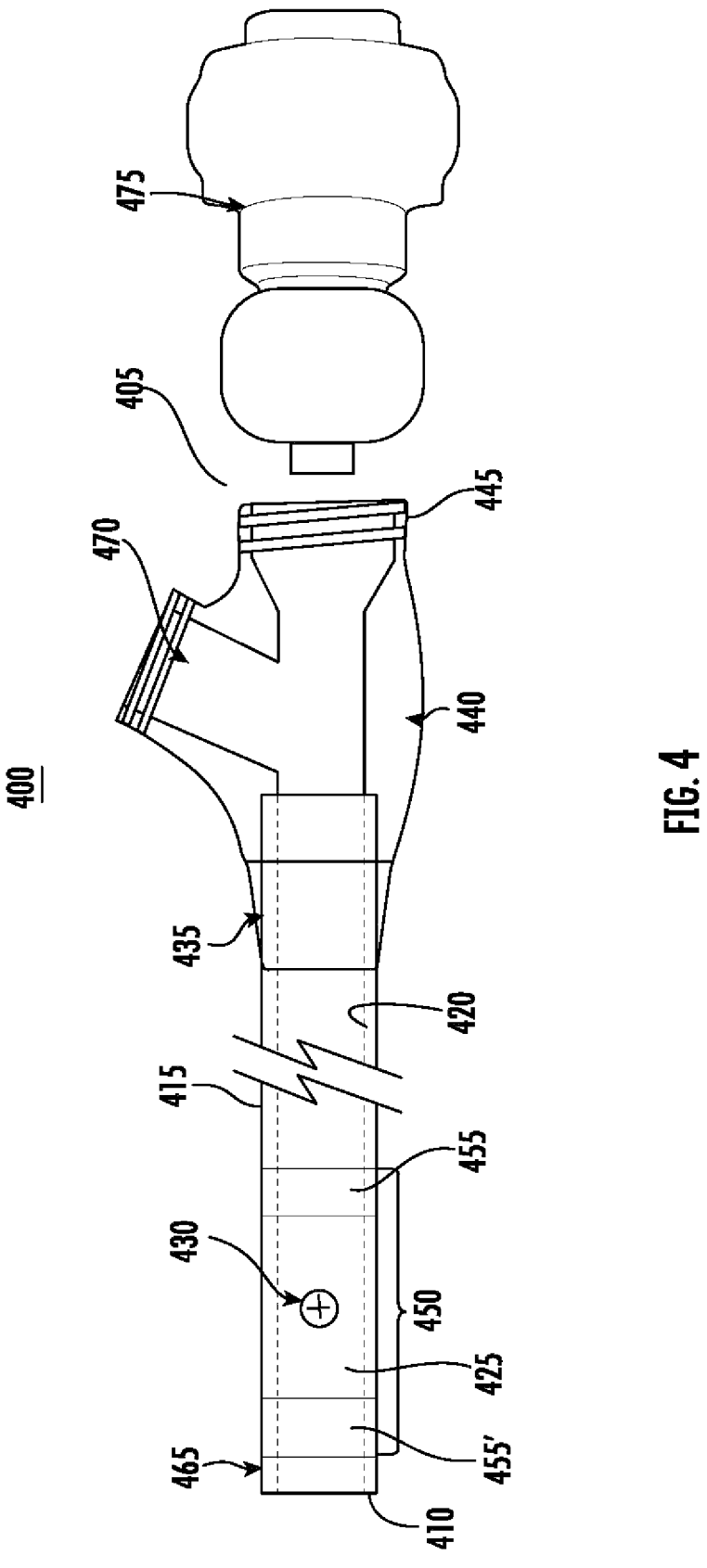
FIG. 4 is a side view of an alternative configuration of the present inventive balloon guide catheter with a single through lumen defined axially/longitudinally therethrough.
Figure 5A:
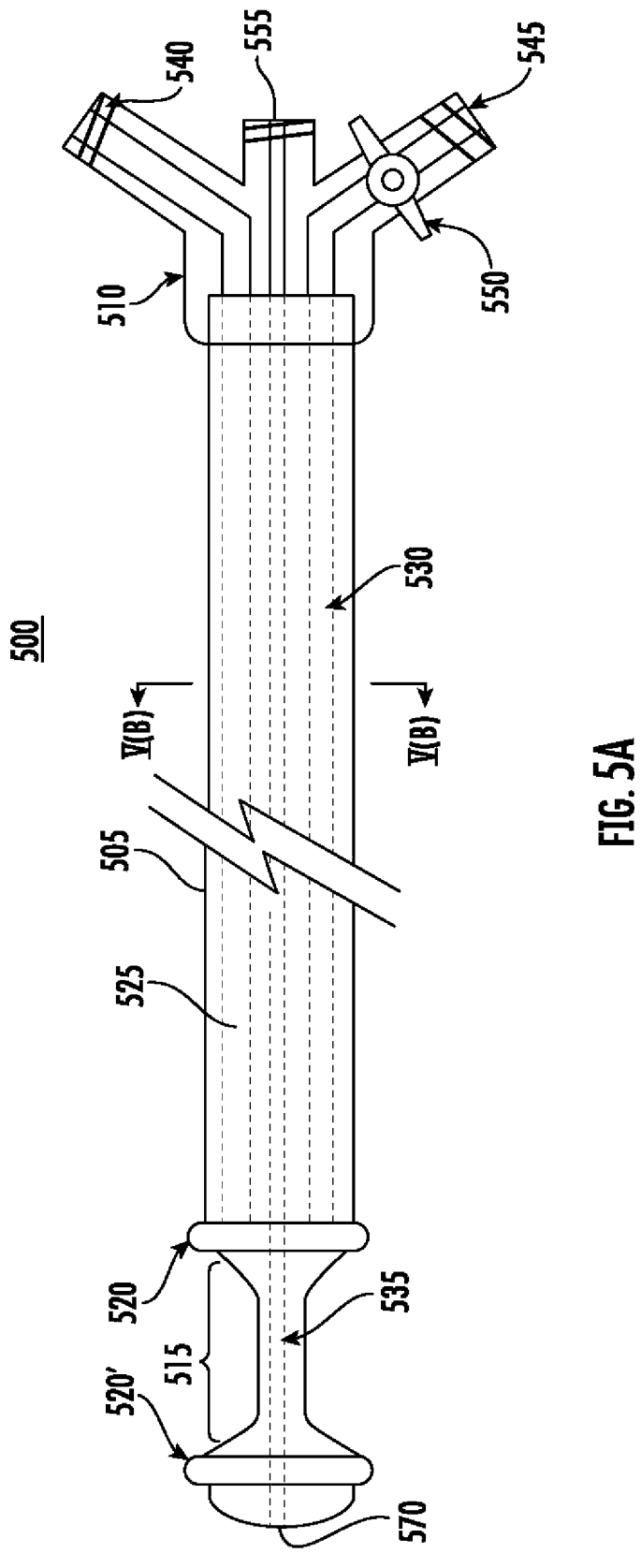
FIG. 5A is a side view of an associated separate, independent, removable fluid conduit device assemblable within the single through lumen of the balloon guide catheter in FIG. 4.
Figure 5B:
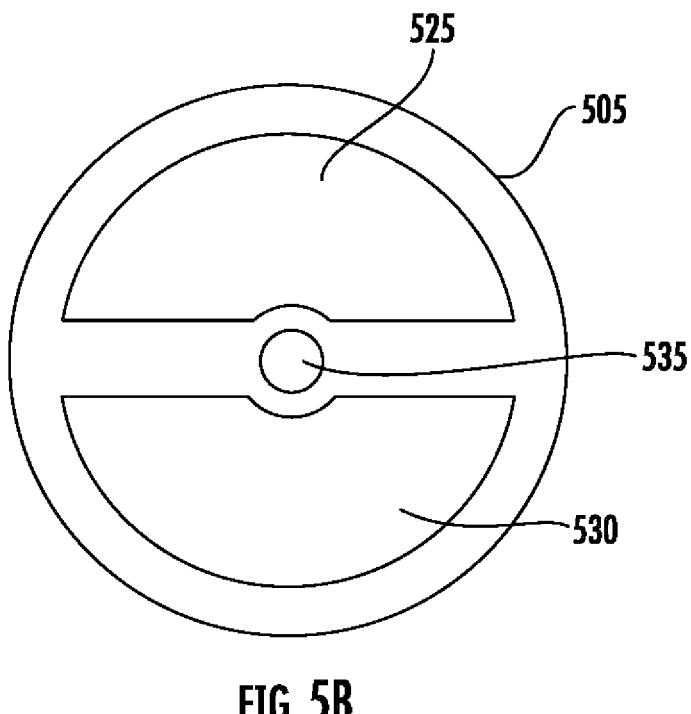
FIG. 5B is a radial cross-sectional view of the shaft member of the removable fluid conduit device of FIG. 5A along lines V(B)-V(B)
Figure 6:
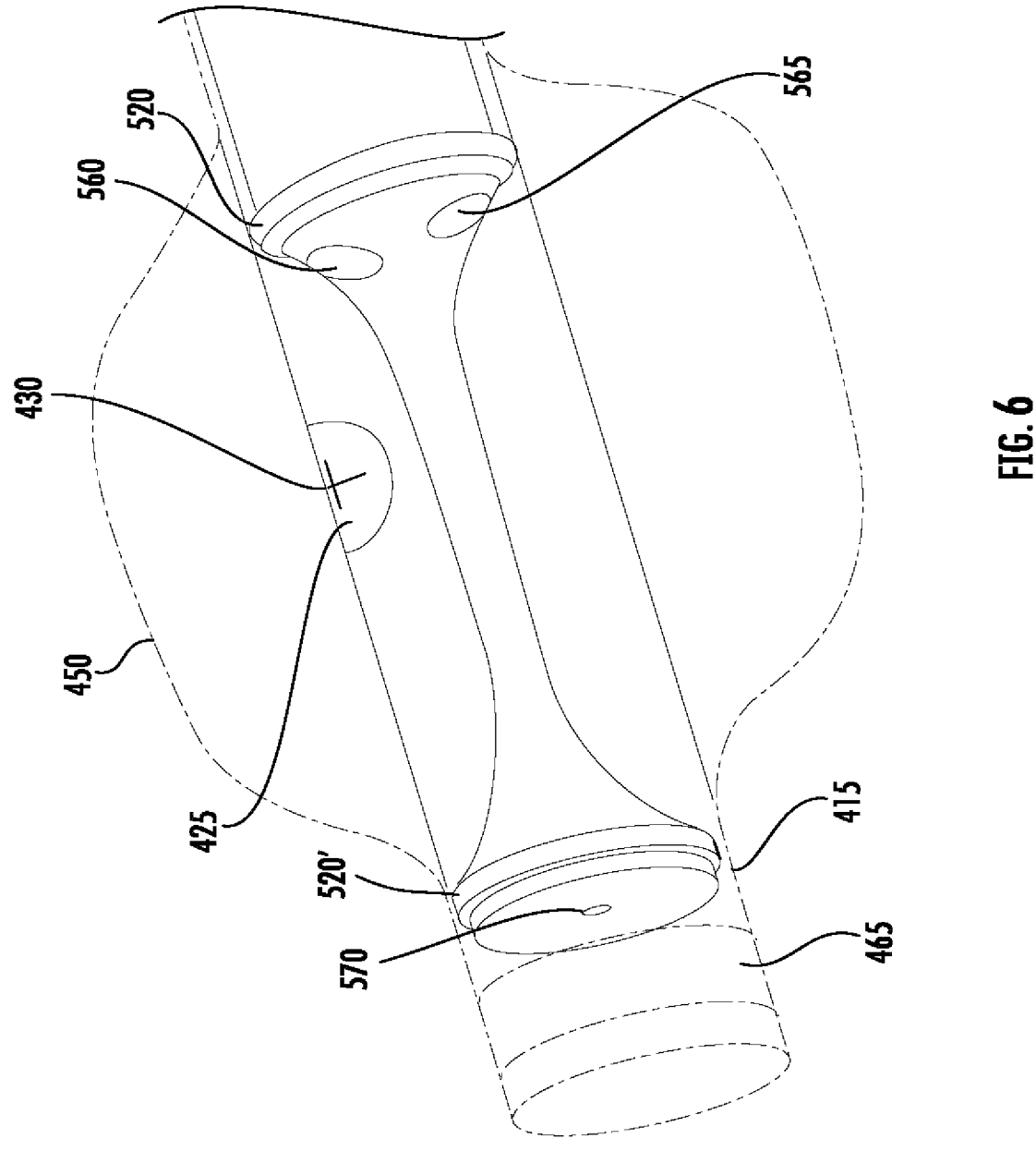
FIG. 6 is a perspective view of the distal end of the separate, independent, removable fluid conduit device of FIG. 5A assembled in the single through lumen of the balloon guide catheter of FIG. 4, wherein the balloon is depicted in an inflated state.

The balloon guide catheter 400 of FIG. 4 is used with the separate, independent, removable fluid conduit device 500 in FIG. 5A that in this particular design has a narrowed or reduced diameter section 515 proximate a distal end of the shaft member 505. The narrowed or reduced diameter section 515 resembling that of a dumbbell in an axial/longitudinal direction when viewed from the side. In an axial/longitudinal direction, the reduced diameter section 515 is flanked on respective proximal and distal ends by sealing rings 520, 520' (e.g., bulbous lips protruding radially outward exceeding in diameter that of the remaining proximal section of the shaft member 505). When the removable fluid conduit device 500 is assembled in the single through lumen 420 of the catheter shaft 415 of the balloon guide catheter 400, the sealing rings 520, 520' create a fluid tight cavity/chamber bounded on respective proximal and distal sides of the opening 430 in the membrane valve 425. In the example shown, the separate, independent, removable fluid conduit device 500 has three axial/longitudinal lumen defined therein: (i) a first lumen 525 for accommodating inflation media (e.g., 50:50 radiopaque contrast agent and saline solution); (ii) a second lumen 530 which either alone or in combination with the first lumen 525 allows for expedient deflation of the balloon 450 of the balloon guide catheter 400; and (iii) a third lumen 535 able to accommodate (track over) a support device therein (e.g., a guidewire and/or stent retriever shaft). FIG. 5B is a radial cross-sectional view through the three lumen of shaft member 505 along lines V(B)-V(B). The first lumen 525 is in fluid communication with a first luer connection 540 of a device hub 510. In similar fashion, second lumen 530 is also in fluid communication with a second luer connection 545 of the device hub 510 having a rotating valve 550 for allowing or prohibiting passage of a fluid therethrough. The first and second lumen 525, 530 have respective distal openings 560, 565 in fluid communication with a region defined radially outward of the narrowed/reduced diameter section 515 of the shaft member 505 (FIG. 6). Still further the separate, independent, removable fluid conduit device 500 includes a third lumen 535. At its proximal end, the third lumen 535 has a third luer connection 555 for connecting accessories thereto. The third lumen 535 extends in an axis/longitudinal direction through/across the narrow/reduced diameter section 515 terminating in a distal opening 570 at the distal end/tip of the shaft member 505.

Proper alignment in an axial direction of the two devices is realized when the separate, independent, removable fluid conduit device 500 is fully inserted into the balloon guide catheter 400. That is, when the hub 510 of the separate, independent, removable fluid conduit device 500 directly physically contacts the removable Tuohy Borst adapter/valve 475 connected to the hub 440 of the balloon guide catheter, commonly known as "hubing-out." Proper positioning in this manner ensures the sealing rings 520, 520' are located on either side of opening 430 in the membrane valve 425 integrated in or secured to the outer wall of the catheter shaft 415 of the balloon guide catheter 400. FIG. 6 depicts a distal section of the assembly of the separate, independent, removable fluid conduit device 500 properly positioned within the single through lumen 420 of the catheter shaft 415 of the balloon guide catheter 400, wherein the balloon 450 is depicted in an inflated state. In this particular configuration in FIGS. 4-6, use of complementary alignment markers to denote when the two devices are properly aligned axially with one another has been eliminated.

In a distal direction, the present inventive separate, independent, removable fluid conduit device 500 is introduced into the single through lumen 420 via the proximal end 405 of the catheter shaft 415 of the balloon guide catheter 400. The two devices are properly aligned in an axial/longitudinal direction when the separate, independent, removable fluid conduit device 500 is fully inserted into the single through lumen 420 of the balloon guide catheter 400. No radial alignment among the two devices is necessary in this particular design.

In an exemplary use, the interventionalist delivers the balloon guide catheter 400 to a vascular occlusion using conventional techniques and support devices (e.g., dilators, introducer sheaths, etc.). A microcatheter and guidewire are introduced through the single through lumen 420 of the balloon guide catheter 400 and across the occlusion. Following withdraw of the guidewire, a stent retriever is advanced through the single through passageway of the microcatheter traversing the clot. The microcatheter is fully withdrawn unsheathing the stent retriever which automatically deploys across the clot. Over a predetermined time period (e.g., approximately 3 minutes to approximately 5 minutes), the occlusion embeds in the stent retriever, during which the separate, independent, removable fluid conduit device 500 is advanced via the single through lumen 420 of the catheter shaft 415 of the balloon guide catheter 400, tracking over the shaft of the stent retriever maintained in position therein, received in the third lumen 535. It is noted that the present invention is suitable for use during a thrombectomy procedure in which capture and retrieval of the target occlusion is exclusively via aspiration (i.e., without use of a mechanical thrombectomy device). In such use, during insertion in the single through lumen 420 of the catheter shaft 415 the separate, independent, removable fluid conduit device 500 would not track over any support device.

The separate, independent, removable fluid conduit device 500 is advanced in a distal direction within the single through lumen 420 of the catheter shaft 415 until fully inserted. In the particular example illustrated in FIGS. 4, 5A, 5B & 6, alignment occurs when the separate, independent, removable fluid conduit device 500 is fully inserted into the single through lumen 420 of the catheter shaft 415 of the balloon guide catheter 400. Fully inserting the removable fluid conduit device ensures that sealing rings 520, 520' form a fluid tight seal on respective proximal and distal sides of the opening 430 in the membrane valve 425 creating a hermetically sealed chamber or cavity for receiving the injected inflation media (as illustrated in FIG. 6).

Prepping of the separate, independent, removable fluid conduit device 500 occurs while the rotating valve 550 associated with the second lumen 530 is in an open state or position allowing the passage of inflation media therethrough. Specifically, inflation media is injected (e.g., via a syringe) connected to the first luer 540 and passing through the first lumen 525, filling the region (i.e., hermetically sealed cavity or chamber) radially outward of the reduced diameter section 515 of the shaft member 505 and thereby positively venting or purging the residual air from the system via the second lumen 530 and out from the second luer 545. A vacuum source, i.e., a syringe, may be connected to the second luer 545 to assist with the purging process. The emergence of inflation media from the second luer 545 being indicative of the residual air having been fully purged from the separate, independent, removable fluid conduit device 500 at which point the interventionalist may transition the rotating valve 550 to a closed state (i.e., preventing passage of fluid therethrough). Prepping or purging of residual air from the fluid conduit device 500 is described above as taking place after insertion into the balloon guide catheter 400. However, it is also contemplated for only one of the fluid lumens in the fluid conduit device 500 to be prepped prior to insertion into the balloon guide catheter 400, while completion of the prepping of the other fluid lumen and hermetically sealed chamber occurs following insertion.

With the rotating valve 550 in a closed state, the continued injection of the inflation media through the first lumen 525 increases the pressure applied on the membrane valve 425 causing the opening 430 defined therein to open radially outwards allowing the inflation media to flow therethrough and inflate the balloon 450, resulting in vascular flow arrest (i.e., occluding blood flow). As the balloon 450 expands/inflates to compensate for the increase in pressure due to further injection of inflation media, the pressure in the system equalizes causing the opening 430 to close. Once the opening 430 has closed, the separate, independent, removable fluid conduit device 500 may be fully removed while the balloon 450 remains inflated. After capture and removal of the occlusion with the stent retriever and/or aspiration, the separate, independent, removable fluid conduit device 500 is reintroduced (following the steps described above during initial insertion). While the rotating valve 550 is in an open state, the balloon 450 is deflated by applying a negative pressure (e.g., vacuum) preferably to both the first and second lumen 525, 530 via respective luers 540, 545. Negative pressure preferably being applied simultaneously to both the first and second lumen 525, 530 to minimize deflation time; however, it is contemplated and within the intended scope of the present invention to apply negative pressure to only one lumen. The negative pressure produced in the region radially outward of the reduced diameter section 515 of the shaft member 505 causes the leaflets of the opening 430 of the membrane valve 425 to open radially inwards allowing the inflation media to escape from and deflate the balloon 450, restoring vascular flow.

Yet another configuration of the present inventive independent, removable, separate fluid conduit device 700 is shown in FIGS. 7A-7E. This particular embodiment combines some of the features associated with previously described designs. For instance, this configuration has an open channel/groove/furrow running in an axial/longitudinal direction along the shaft member section (similar to that of the configuration in FIGS. 2A-2C) allowing the removable fluid conduit device to be tracked over a support device (e.g., microcatheter, stent retriever shaft and/or guidewire). In addition, the separate, independent, removable fluid conduit device 700 of FIGS. 7A-7E forms a hermetically sealed cavity or chamber against the inner wall of the single through lumen of the catheter shaft of the balloon guide catheter into which it is assembled (similar to that of the other configuration in FIGS. 4-6).

Figure 7A:
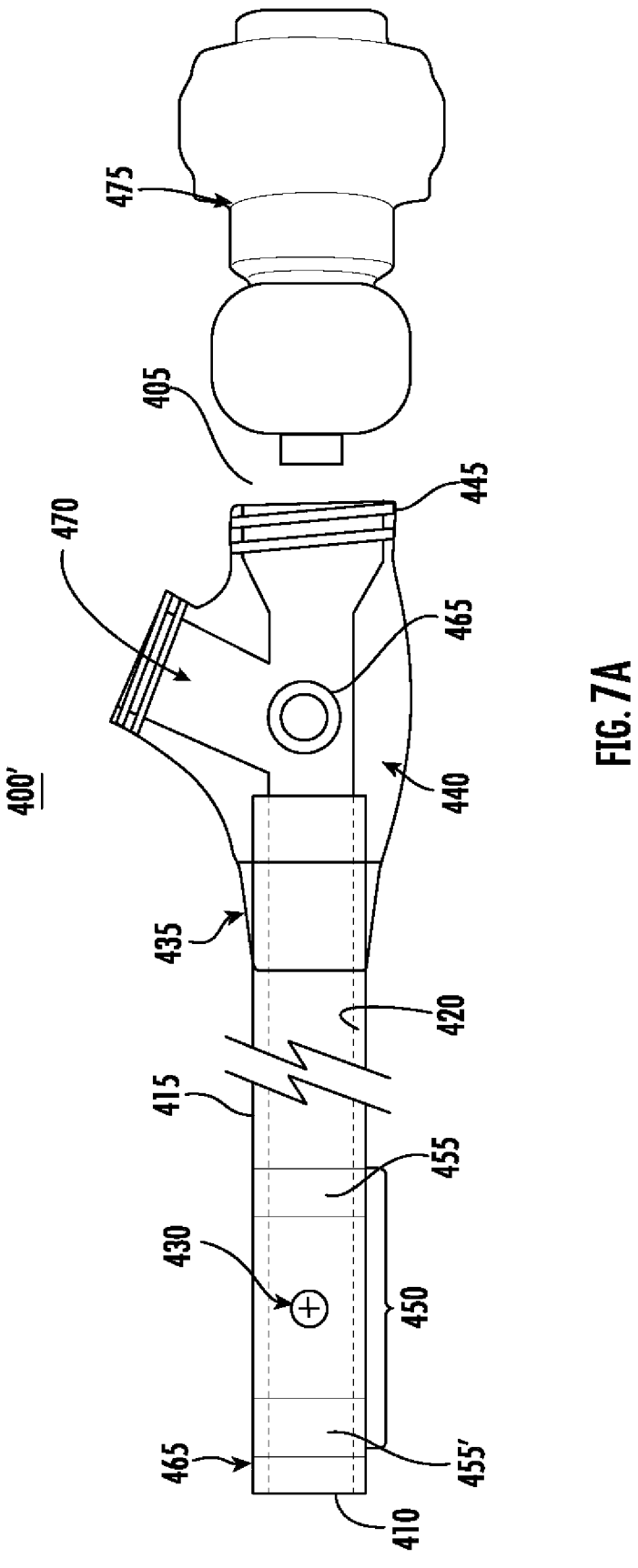
FIG. 7A is a side view of the balloon guide catheter of FIG. 4 modified to include an alignment indicator ring.
Figure 7B:
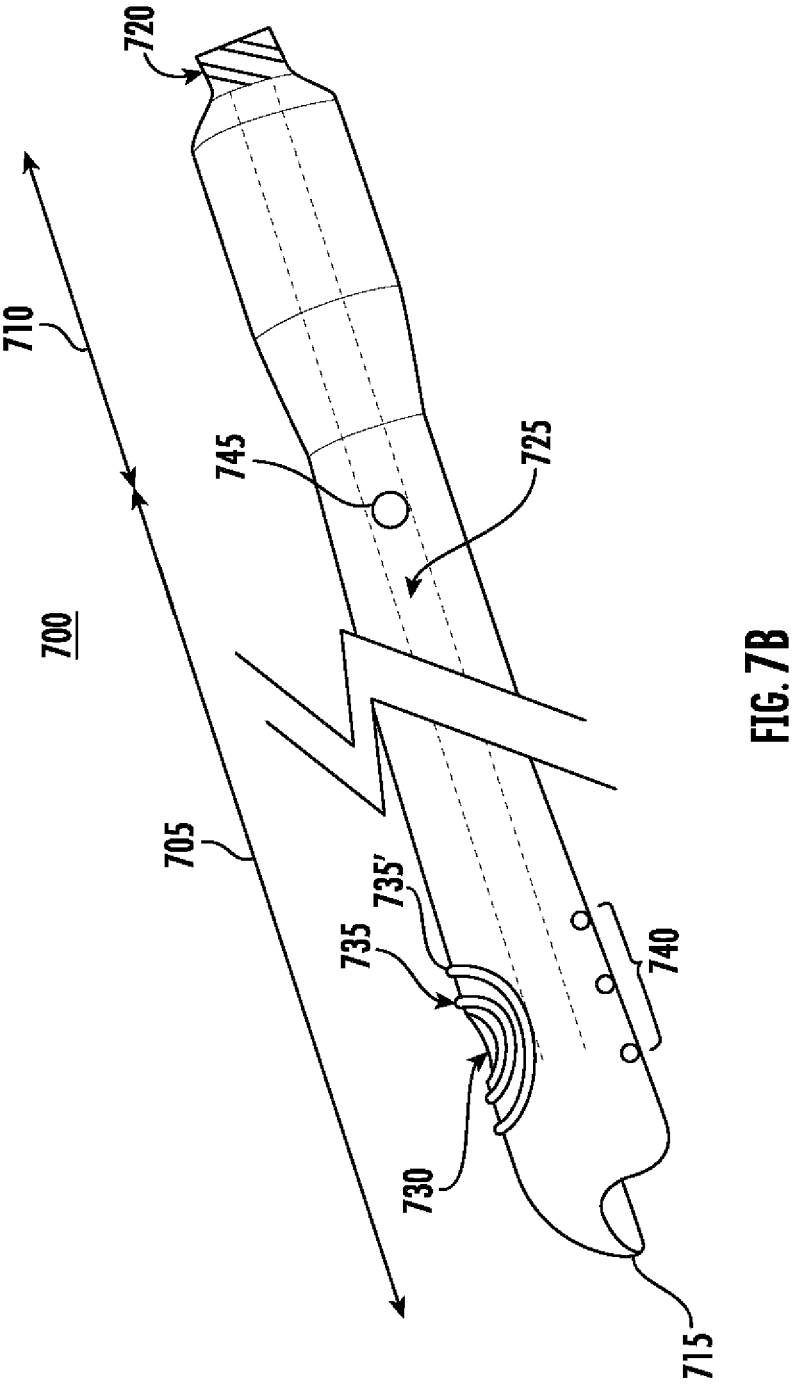
FIG. 7B is a perspective view of yet another configuration of the present inventive separate, independent, removable fluid conduit device to be employed with the configuration of the balloon guide catheter of FIG. 7A wherein the view shown is downward on the side exit opening of the fluid lumen, wherein the side exit opening is arranged radially opposite a center of the longitudinal open channel/groove/furrow receiving therein the microcatheter and/or guidewire.
Figure 7C:
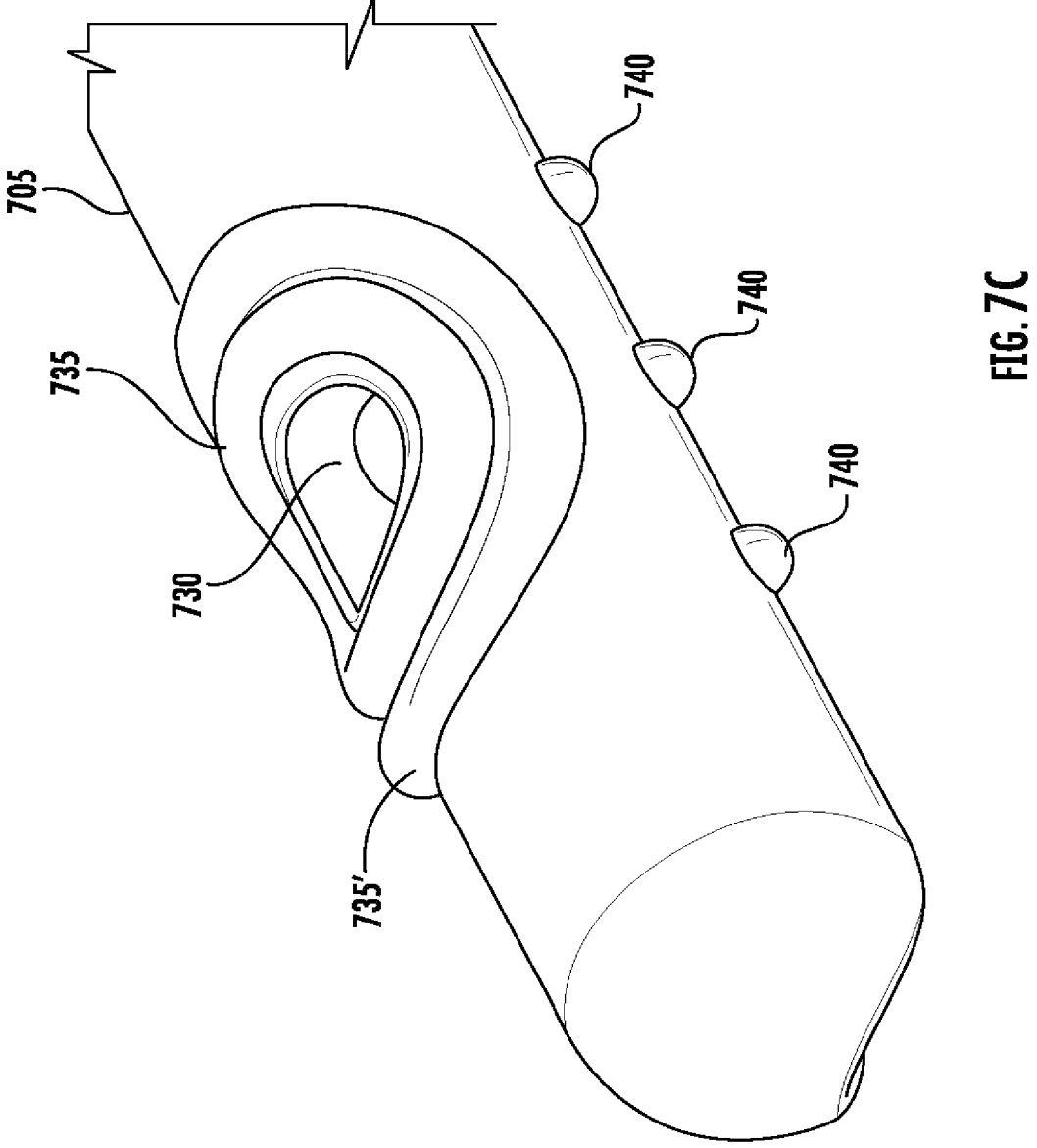
FIG. 7C is an enlarged partial view of the side exit opening of the fluid lumen in a distal section of the separate, independent, removable fluid conduit device of FIG. 7B.
Figure 7D:
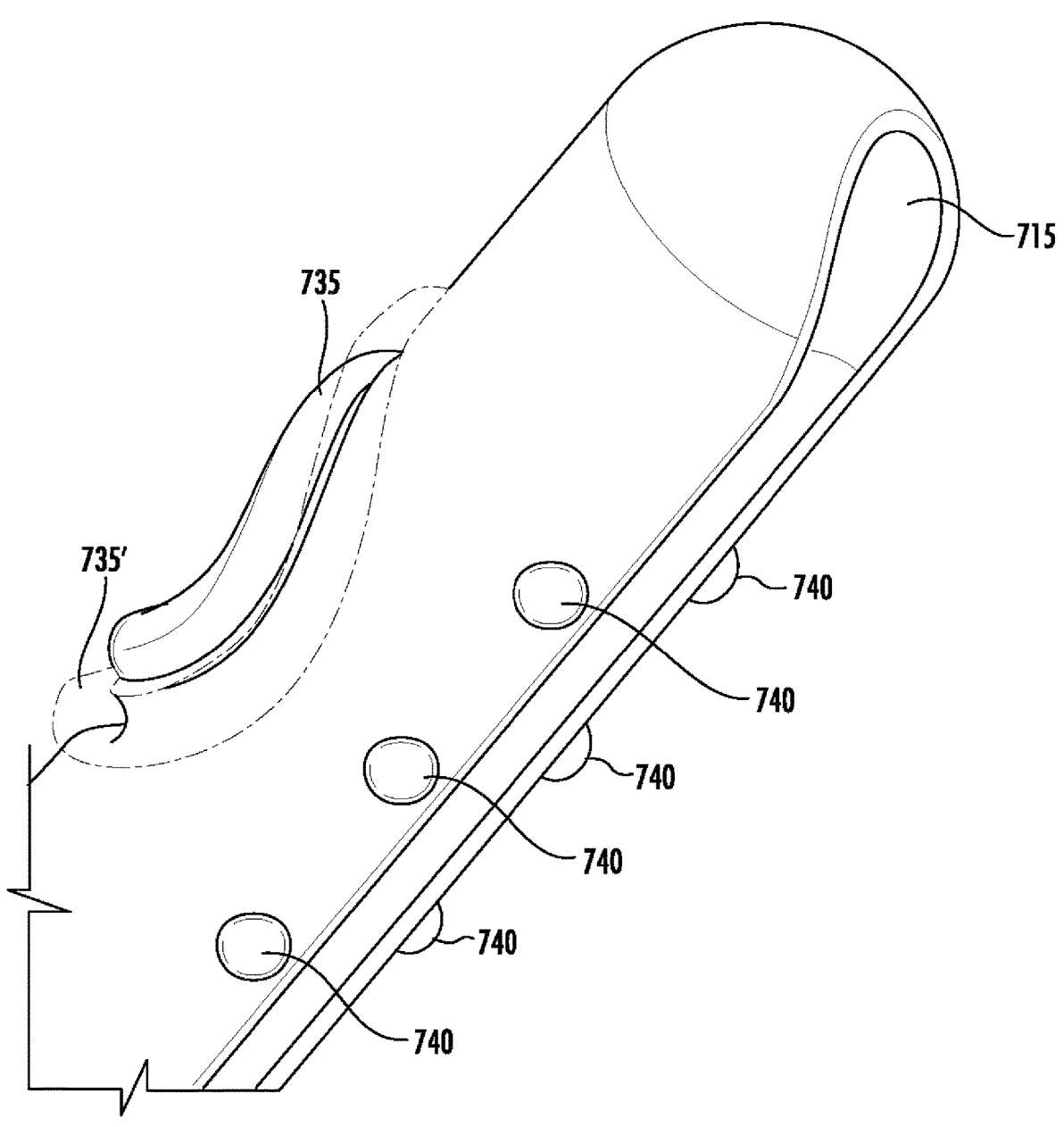
FIG. 7D is an enlarged perspective view of a distal section of the separate, independent, removable fluid conduit device of FIG. 7B, wherein the view shown is upward on the longitudinal open channel/groove/furrow for receiving the microcatheter and/or guidewire therein.
Figure 7E:
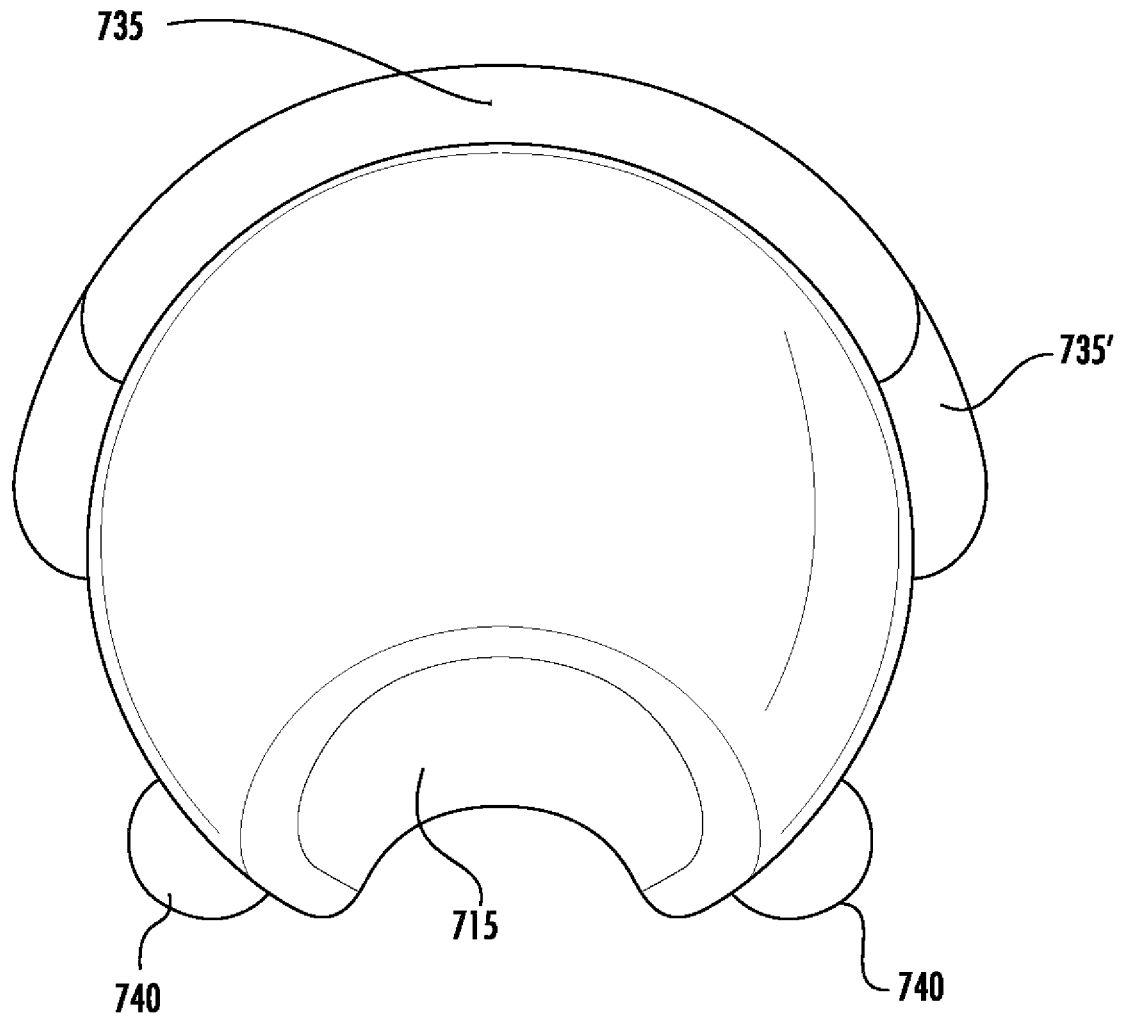
FIG. 7E is an enlarged distal end view of the separate, independent, removable fluid conduit device of FIG. 7B.

FIG. 7A depicts a modified configuration of the balloon guide catheter 400', similar to that in FIG. 4 except for inclusion of an alignment marker to ensure proper alignment both radially and axially/longitudinally therein of a separate, independent, removable fluid conduit device 700, shown in FIG. 7B. Starting at the proximal end and moving towards the opposite distal end, the separate, independent, removable fluid conduit device 700 includes a luer connection 720, a device hub 710 and a shaft member 705. A single open curved channel/groove/furrow 715 extends in an axial/longitudinal direction along the shaft member 705 forming a crescent shape radial cross-section. Similar to that of the first configuration in FIGS. 2A-2D, the open channel/groove/furrow 715 feature in this design of the separate, independent, removable fluid conduit device 700 is trackable over a support device (e.g., microcatheter, shaft of a stent retriever and/or guidewire) while maintained in the single through lumen 420 of the balloon guide catheter 400' without having to be removed. Shaft member 705 has an inflation lumen 725 defined therein whose side exit opening 730 is located on the outer wall of the shaft member 705. Preferably, the side exit opening 730 is radially opposite (e.g., approximately 180°) a center of the single open channel/groove/furrow 715. One or more sealing ring(s) 735, 735' (e.g., an O-ring) is disposed concentrically about the perimeter of the side exit opening 730 of the inflation lumen 725. A plurality of raised projections 740 (e.g., raised hemispherical projections) are arranged on the outer surface of the shaft member 705 not forming part of but proximate to the single open channel/groove/furrow 715. For example, in FIG. 7B-7E, the raised projections 740 are located on parallel "lips" extending in an axial/longitudinal direction forming each side of the single open groove/channel/furrow 715 and radially opposite (e.g., 180°) the side exit opening 730 of the inflation lumen 725 (FIGS. 7B & 7C). When the components are assembled, the projections 740 physically contact the inner wall of the single through lumen 420 of the catheter shaft 415 of the balloon guide catheter 400' lifting/raising the shaft member 705 of the separate, independent, removable fluid conduit device 700 therein creating a tighter seal between the concentric sealing rings 735, 735' and the membrane valve 425 of the catheter shaft 415 of the balloon guide catheter 400'. Optionally, the projections 740 may be eliminated.

Proper alignment of the separate, independent, removable fluid conduit device 700 in the balloon guide catheter 400' is achieved using complementary alignment markers. By way of illustrative example, in FIG. 7A the balloon guide catheter 400' includes an alignment marker in the shape of an open (i.e., non-filled in) ring or circle 465 on the outer wall of the catheter hub 440. While FIG. 7B shows the separate, independent, removable fluid conduit device 700 having an alignment marker in the complementary shape of filled in or solid circle disposed on the outer wall of the shaft member 705. The alignment marker 745 associated with the separate, independent, removable fluid conduit device 700 has a diameter less than or equal to that of the opening in the circle (ring) alignment marker 465 of the balloon guide catheter 400'. Alignment markers 465, 745 may be printed, painted or adhered to the outer surface of the hub 440 or shaft member 705, respectively. Catheter hub 440 is preferably manufactured from a transparent plastic material, e.g., polycarbonate. During the procedure, the catheter hub 440 remains outside the body while the separate, independent, removable fluid conduit device 700 is inserted in the single through lumen 120 of the catheter shaft 415 until the two components are visually properly aligned both axially and radially. That is, proper alignment, both axially and radially, of the two components is realized when the filled in circle alignment marker 745 associated with the separated, independent, removable fluid conduit device 700 is disposed within the open or ring (non-filled) circle alignment marker 465 located on the catheter shaft 415 of the balloon guide catheter 400'. The shapes or configurations of the complementary alignment markers associated with each of the removable fluid conduit device and associated balloon guide catheter may be configured, as desired, to denote proper positioning among the two assembled components when the respective markers are visually aligned in position with each other.

Typically employing a conventional introducer sheath (not shown), the interventionalist introduces the balloon guide catheter 400' (FIG. 7A) into the body, typically, via the femoral artery and navigates to the target site. A microcatheter and guidewire (together with any other conventional support devices) is introduced into the single through lumen 420 of the balloon guide catheter 400'. Next, either simultaneously or sequentially one after the other, the target occlusion is traversed with the guidewire in combination with the microcatheter. Whereafter, the guidewire is fully withdrawn and the stent retriever is delivered through the microcatheter. The microcatheter is then partially withdrawn unsheathing the stent retriever which remains stationary. As it is unsheathed from the microcatheter, the stent retriever automatically deploys across the clot which over passage of a predetermined period of time becomes embedded therein. Outside the body, before assembly in the single through lumen 420 of the balloon guide catheter 400', the separate, independent, removable fluid conduit device 700 is prepped by positively venting residual air from the fluid lumen (e.g., inflation lumen) 725. Specifically, a syringe is connected to the luer connection 720 and a fluid (e.g., inflation media, typically a 50:50 solution of radiopaque contrast agent and saline solution) is injected into the fluid lumen 725 (e.g., inflation lumen) until the residual air is discharged from its side exit opening 730. So long as the balloon 450, while in a deflated state, is hermetically sealed to the outer surface of the catheter shaft then the balloon guide catheter 400' itself need not be prepped (i.e., purged of residual air).

Once prepped, the independent, removable, separate fluid conduit device 700 is inserted into the single lumen 420 of the balloon guide catheter 400'. That is, while maintaining the microcatheter in position (i.e., without withdrawal of the microcatheter) the fluid conduit device 700 is advanced in a distal direction through the single through lumen 420 of the balloon guide catheter 400' tracking over the microcatheter received within the single axial/longitudinal open channel/ groove/furrow 715. The separate, independent, removable fluid conduit device 700 is advanced in a distal direction through the single lumen 420 of the balloon guide catheter 400' until the two components are properly aligned, i.e., when the sealing rings 735, 735' disposed about the side exit opening 730 of the fluid conduit device 700 encircles the opening 430 while forming a hermetic seal against the membrane valve 425. Such proper alignment among the two components is visually observed by the interventionalist when the alignment markers 465, 745 associated with each of the balloon guide catheter 400' and the separate, independent, removable fluid conduit device 700 coincide/align with one another. By way of illustrative example, alignment both axially/longitudinally and radially of the two devices is realized when alignment marker 745 associated with the separate, independent, removable fluid conduit device 700 coincides with (e.g., positioned within) the open ring alignment marker 465 of the balloon guide catheter 400'. With the two devices in a state of proper alignment, the fluid (e.g., inflation media) passing through the inflation lumen 725 of the fluid conduit device 700 enters through the opening 430 in the membrane valve 425 and inflates the balloon 450. Once the balloon 450 is inflated, the separate, independent, removable fluid conduit device 700 is fully removed from the balloon guide catheter 400'. Post vascular recanalization, the separate, independent, removable fluid conduit device 700 is reintroduced into balloon guide catheter 400', realigned (repeating the same procedural steps described above), and a vacuum source is applied to the inflation lumen 725 via the luer connection 720 to remove the inflation media causing the balloon 450 to deflate.

Features associated with each configuration of the balloon guide catheter and/or separate fluid conduit device may be modified or combined, as desired. Furthermore, the present inventive intravascular catheter with which the present inventive separate, independent, removable fluid conduit device is used may not include a balloon, i.e., need not necessarily be a balloon guide catheter. In such case the "fluid" delivered by the present inventive separate fluid conduit device would be something other than an inflation media (e.g., contrast saline solution) perhaps a contrasting agent used during imaging or any other type of "fluid."

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An assemblable device comprising:

an intravascular catheter including a catheter shaft having an outer wall defining a single through lumen from a proximal end to an opposite distal end; proximate the distal end a portion of the outer wall of the catheter shaft is a membrane valve with an opening defined therein; and a separate, independent, removable fluid conduit device having a fluid lumen defined therein; the separate, independent, removable fluid conduit device is assemblable so as to be slidable in the single through lumen of the intravascular catheter, wherein the separate, independent, removable fluid conduit device comprises:

a shaft member having a passageway defined therein from a proximal end to an opposite distal end; the shaft member further including a tapered inner diameter distal section and an open channel extending in a longitudinal direction defined along an outer wall of the shaft member from the proximal end to the tapered inner diameter distal section;

an extendable fluid lumen having a tapered outer diameter distal section; the extendable fluid lumen being slidable within the passageway of the shaft member between a first state in which the tapered outer diameter distal section of the extendable fluid lumen is entirely sheathed within the passageway of the shaft member and a second state in which the tapered outer diameter distal section of the extendable fluid lumen is completely unsheathed from the shaft member; wherein the tapered outer diameter distal section of the extendable fluid lumen bends or curves in the second state;

wherein the intravascular catheter has associated therewith a first alignment marker and the shaft member of the separate, independent, removable fluid conduit device has associated therewith a second alignment marker; wherein the arrangement of the first and second alignment markers is such that in a state of proper alignment both longitudinally and radially of the shaft member of the separate, independent, removable fluid conduit device in the single through lumen of the intravascular catheter, the distal tip of the tapered outer diameter distal section of the extendable fluid lumen directly physically engages the opening in the membrane valve when positioned in the second state, and wherein the first alignment marker is a partial radial band extending less than 360 radially about the intravascular catheter and the second alignment marker is a complementary partial radial band extending less than 360 degrees radially about the shaft member of the separate, independent, removable fluid conduit device; and in the state of proper alignment the first and second alignment markers together form a 360° radial band.

2. The assemblable device according to claim 1, wherein the intravascular catheter is a balloon guide catheter with a balloon covering the opening in the membrane valve and secured about an outer surface of the outer wall of the catheter shaft.

3. A method for using an assemblable device comprising a balloon guide catheter including a catheter shaft having an outer wall defining a single through lumen from a proximal end to an opposite distal end; proximate the distal end a portion of the outer wall of the catheter shaft is a membrane valve with an opening defined therein; the membrane valve being covered by a balloon secured to an outer surface of the outer wall of the catheter shaft; the assemblable device further including a separate, independent, removable fluid conduit device having a fluid lumen defined therein; the separate, independent, removable fluid conduit device is assemblable so as to be slidable in the single through lumen of the balloon guide catheter; the method comprising the steps of:

navigating the balloon guide catheter to a position proximal a target occlusion;

inserting the separate, independent, removable fluid conduit device into the single through lumen of the balloon guide catheter; wherein before and/or after insertion into the balloon guide catheter the separate, independent, removable fluid conduit device is prepped to purge residual air from the fluid lumen;

properly aligning the separate, independent, removable fluid conduit device within the balloon guide catheter;

injecting the inflation media via the fluid lumen, through the opening of the membrane valve and into the balloon; and withdrawing the separate, independent, removable fluid conduit device, wherein the shaft member of the separate, independent, removable fluid conduit device has a passageway defined therein from a proximal end to an opposite distal end; the shaft member further including a tapered inner diameter distal section and a single open channel extending in a longitudinal direction defined along the outer wall of the shaft member from the proximal end to the tapered inner diameter distal section trackable over a microcatheter; and the separate, independent, removable fluid conduit device further comprises an extendable fluid lumen having a tapered outer diameter distal section; the extendable fluid lumen being slidable within the passageway of the shaft member between a first state in which the tapered outer diameter distal section of the extendable fluid lumen is entirely sheathed within the passageway of the shaft member and a second state in which the tapered outer diameter distal section of the extendable fluid lumen is completely unsheathed from the shaft member; wherein the tapered inner diameter distal section of the shaft member is sized to deflect the tapered outer diameter distal section of the extendable fluid lumen when advanced therethrough in a distal direction; and wherein the balloon guide catheter has associated therewith a first alignment marker and the shaft member of the separate, independent, removable fluid conduit device has associated therewith a second alignment marker; wherein the proper aligning step comprises in a state of proper alignment both longitudinally and radially of the first and second alignment markers, a distal tip of the tapered outer diameter distal section of the extendable fluid lumen directly physically engages the opening in the membrane valve when positioned in the second state, and wherein the first alignment marker is a partial radial band extending less than 360° radially about the balloon guide catheter and the second alignment marker is a complementary partial radial band extending less than 360 degrees radially about the shaft member of the separate, independent, removable fluid conduit device; and in the state of proper alignment the first and second alignment markers together form a 360° radial band.

4. The method according to claim 3, further comprising the steps of:

reintroducing the separate, independent, removable fluid conduit device into the single through lumen of the balloon guide catheter; wherein either before and/or after reintroduction into the balloon guide catheter the separate, independent, removable fluid conduit device is prepped to purge residual air from the fluid lumen;

properly aligning the separate, independent, removable fluid conduit device within the balloon guide catheter;

applying a negative pressure to the fluid lumen of the separate, independent, removable fluid conduit device causing the inflation media to be withdrawn and the balloon to deflate; and withdrawing the separate, independent, removable fluid conduit device from the balloon guide catheter.

5. The method according to claim 3, wherein prior to the inserting step, further comprising the steps of:

via the single through lumen of the balloon guide catheter, navigating as a single unit a guidewire disposed in a microcatheter;

capturing the target occlusion by: (i) deploying a stent retriever from the microcatheter; and/or (ii) applying a vacuum to the microcatheter.

6. A method for using an assemblable device comprising an intravascular catheter including a catheter shaft having an outer wall defining a single through lumen from a proximal end to an opposite distal end; proximate the distal end a portion of the outer wall of the catheter shaft is a membrane valve with an opening defined therein; the assemblable device further including a separate, independent, removable fluid conduit device having a fluid lumen defined therein; the separate, independent, removable fluid conduit device is assemblable so as to be slidable in the single through lumen of the intravascular catheter; the method comprising the steps of:

navigating the intravascular catheter to a target site;

inserting the separate, independent, removable fluid conduit device into the single through lumen of the intravascular catheter;

properly aligning the separate, independent, removable fluid conduit device within the intravascular catheter;

injecting the fluid media via the fluid lumen, through the opening of the membrane valve; and withdrawing the separate, independent, removable fluid conduit device, wherein the shaft member of the separate, independent, removable fluid conduit device has a passageway defined therein from a proximal end to an opposite distal end; the shaft member further including a tapered inner diameter distal section and a single open channel extending in a longitudinal direction defined along the outer wall of the shaft member from the proximal end to the tapered inner diameter distal section trackable over a microcatheter; and the separate, independent, removable fluid conduit device further comprises an extendable fluid lumen having a tapered outer diameter distal section; the extendable fluid lumen being slidable within the passageway of the shaft member between a first state in which the tapered outer diameter distal section of the extendable fluid lumen is entirely sheathed within the passageway of the shaft member and a second state in which the tapered outer diameter distal section of the extendable fluid lumen is completely unsheathed from the shaft member; wherein the tapered inner diameter distal section of the shaft member is sized to deflect the tapered outer diameter distal section of the extendable fluid lumen when advanced therethrough in a distal direction; and wherein the balloon guide catheter has associated therewith a first alignment marker and the shaft member of the separate, independent, removable fluid conduit device has associated therewith a second alignment marker; wherein the proper aligning step comprises in a state of proper alignment both longitudinally and radially of the first and second alignment markers, a distal tip of the tapered outer diameter distal section of the extendable fluid lumen directly physically engages the opening in the membrane valve when positioned in the second state, and wherein the first alignment marker is a partial radial band extending less than 360° radially about the balloon guide catheter and the second alignment marker is a complementary partial radial band extending less than 360 degrees radially about the shaft member of the separate, independent, removable fluid conduit device; and in the state of proper alignment the first and second alignment markers together form a 360° radial band.

\* \* \* \* \*